US011752510B2

(12) United States Patent
Liu et al.

(10) Patent No.: US 11,752,510 B2
(45) Date of Patent: Sep. 12, 2023

(54) FLUID DISPENSER FOR RECOVERING MATERIAL FROM A SURFACE

(71) Applicant: Upside Foods, Inc., Berkeley, CA (US)

(72) Inventors: Ryan Liu, Berkeley, CA (US);
Michelle Warner, Berkeley, CA (US);
Jaewon Samuel Kang, Berkeley, CA (US); Matthew Leung, Berkeley, CA (US); Eric Ordonez, Berkeley, CA (US); Roshan Patel, Berkeley, CA (US); Konrad Muller-Auffermann, Berkeley, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

(21) Appl. No.: 17/647,554

(22) Filed: Jan. 10, 2022

(65) Prior Publication Data

US 2022/0401974 A1 Dec. 22, 2022

Related U.S. Application Data

(63) Continuation of application No. 17/304,271, filed on Jun. 17, 2021.

(51) Int. Cl.
*B05B 3/10* (2006.01)
*B05B 3/04* (2006.01)
(Continued)

(52) U.S. Cl.
CPC ............. *B05B 3/1021* (2013.01); *B05B 3/04* (2013.01); *B05B 3/1057* (2013.01); *B05B 16/00* (2018.02); *C12M 29/06* (2013.01)

(58) Field of Classification Search
CPC ......... B05B 3/1057; B05B 3/04; B05B 16/00; B05B 3/1021; B05B 9/0423; B05B 12/04;
(Continued)

(56) References Cited

U.S. PATENT DOCUMENTS 3,833,173 A    9/1974   Rose et al.
5,241,975 A *   9/1993   Yanagihara ............. A47L 15/23
                                                                                                               134/182
(Continued)

FOREIGN PATENT DOCUMENTS

CN       105349409 A    2/2016
CN       106479883 A    3/2017
(Continued)

OTHER PUBLICATIONS

International Search Report and the Written Opinion for International Application No. PCT/US2021/037786 dated Mar. 15, 2022, 9 pages.
(Continued)

*Primary Examiner* — Tuongminh N Pham
*Assistant Examiner* — Kevin Edward Schwartz
(74) *Attorney, Agent, or Firm* — Keller Preece PLLC

(57) ABSTRACT

An assembly for delivering a fluid includes a fluid dispenser connected to a fluid supply conduit. The fluid dispenser includes a fluid outlet positioned along a length of the fluid dispenser. The fluid outlet is configured to deliver the fluid from the fluid supply conduit at a flow rate that varies along the length of the fluid dispenser.

20 Claims, 13 Drawing Sheets

(51) Int. Cl.
*C12M 1/00* (2006.01)
*B05B 16/00* (2018.01)

(58) Field of Classification Search
CPC . B05B 12/085; B05B 12/087; B05B 12/1208; B05B 1/3073; B05B 3/063; B05B 3/08; B05B 3/085; A22C 17/08; C12M 29/06
USPC .......... 239/381, 66, 68, 76, 551, 553, 553.5, 239/554, 562, 566, 567; 222/547
See application file for complete search history.

(56) References Cited

U.S. PATENT DOCUMENTS

| | | | |
|---|---|---|---|
| 6,245,557 | B1 | 6/2001 | Fouts et al. |
| 6,736,340 | B1* | 5/2004 | Wang .................... B05B 1/3026 239/548 |
| 7,032,604 | B2 | 4/2006 | Welch |
| 7,235,402 | B2 | 6/2007 | Aubry et al. |
| 7,493,907 | B2 | 2/2009 | Roh |
| 7,617,996 | B2 | 11/2009 | Lee |
| 7,629,167 | B2 | 12/2009 | Hodge et al. |
| 8,092,613 | B2* | 1/2012 | Strothoff ................ C11D 3/044 134/28 |
| 8,507,263 | B2* | 8/2013 | Asnaghi ................. C12M 27/10 435/284.1 |
| 9,109,193 | B2 | 8/2015 | Galliher et al. |
| 9,120,111 | B2* | 9/2015 | Nations .................... B05B 15/55 |
| 9,578,885 | B1* | 2/2017 | Glascock .................. A23B 4/12 |
| 9,908,664 | B2 | 3/2018 | Galliher et al. |
| 10,100,408 | B2 | 10/2018 | Ha et al. |
| 10,406,545 | B2* | 9/2019 | Spang, Jr. ........... B05B 11/3023 |
| 10,524,491 | B2 | 1/2020 | Eskamani et al. |
| 10,588,480 | B2* | 3/2020 | Lee ...................... A47L 15/4282 |
| 10,610,080 | B2 | 4/2020 | Dogan et al. |
| 10,889,793 | B2* | 1/2021 | Silverman .............. C12M 29/08 |
| 11,254,902 | B2 | 2/2022 | Wang et al. |
| 2003/0213503 | A1* | 11/2003 | Price .................... C11D 11/007 134/40 |
| 2004/0187898 | A1* | 9/2004 | Chen .................. A47L 15/4234 134/108 |
| 2005/0058013 | A1* | 3/2005 | Warf ....................... A23B 4/26 366/98 |
| 2008/0206735 | A1 | 8/2008 | Asgari |
| 2009/0101185 | A1* | 4/2009 | Pardini ................... A47L 15/23 134/179 |
| 2011/0212493 | A1 | 9/2011 | Hirschel et al. |
| 2011/0266373 | A1 | 11/2011 | Struck et al. |
| 2013/0334344 | A1 | 12/2013 | Leeser |
| 2016/0020074 | A1* | 1/2016 | Mohn ............... C23C 16/45565 239/548 |
| 2016/0138158 | A1* | 5/2016 | Wamura .............. H01J 37/3244 118/728 |
| 2016/0236924 | A1* | 8/2016 | Hortmanns ............... B05B 1/00 |
| 2016/0262371 | A1* | 9/2016 | Hiddema ............. A01M 7/0067 |
| 2017/0216853 | A1* | 8/2017 | Wang ....................... B05B 3/02 |
| 2018/0169682 | A1* | 6/2018 | Miller ................. B05B 17/0607 |
| 2018/0184880 | A1* | 7/2018 | Lee ...................... A47L 15/0018 |
| 2018/0249881 | A1 | 9/2018 | Noriega et al. |
| 2018/0282678 | A1 | 10/2018 | Castillo et al. |
| 2019/0211294 | A1* | 7/2019 | Karnieli ................. C12M 41/12 |
| 2020/0163524 | A1 | 5/2020 | Jung et al. |
| 2020/0243324 | A1 | 7/2020 | Kamakura et al. |
| 2020/0255783 | A1 | 8/2020 | Ferrie et al. |
| 2020/0397213 | A1* | 12/2020 | Kwon .................... A47L 15/23 |
| 2021/0130760 | A1 | 5/2021 | Castillo et al. |
| 2021/0348103 | A1 | 11/2021 | Park |

FOREIGN PATENT DOCUMENTS

| | | | |
|---|---|---|---|
| CN | 107475099 | A | 12/2017 |
| CN | 109294876 | A | 2/2019 |
| CN | 110241023 | A | 9/2019 |
| DE | 19617973 | C1 | 1/1998 |
| EP | 1252856 | A2 | 10/2002 |
| GB | 2019204 | A * | 10/1979 ............ A47L 15/23 |
| WO | WO 2019/122239 | A1 | 6/2019 |
| WO | 2020/243324 | A1 | 12/2020 |
| WO | 2021/102375 | A1 | 5/2021 |
| WO | WO-2022097139 | A1 * | 5/2022 |

OTHER PUBLICATIONS

U.S. Appl. No. 17/304,271, Feb. 7, 2022, Office Action.
U.S. Appl. No. 17/304,271, May 23, 2022, Office Action.
U.S. Appl. No. 17/304,271, Sep. 1, 2022, Office Action.
U.S. Appl. No. 17/304,271, Dec. 13, 2022, Office Action.
U.S. Appl. No. 17/304,271, Mar. 30, 2023, Office Action.
U.S. Appl. No. 14/304,271, Jul. 11, 2023, Notice of Allowance.

* cited by examiner

FLUID DISPENSER FOR RECOVERING MATERIAL FROM A SURFACE

CROSS-REFERENCE TO RELATED APPLICATION

This is a Continuation of U.S. application Ser. No. 17/304,271, filed Jun. 17, 2021, the entire contents of which are incorporated herein by reference.

TECHNICAL FIELD

The present disclosure relates to a fluid dispenser, and more particularly, to a fluid dispenser for recovering material grown on substrates using a flow of a fluid.

BACKGROUND

Lab-grown or cultured meat belongs to the emerging field of cellular agriculture and represents a promising technology for delivering products that have so far been produced through livestock. This technological innovation aims to offer a possibility of reducing the negative effects of conventional meat production techniques on humans, livestock, and the environment. The production of cultured meat requires suitable cells and appropriate growth media. Cultured meat could also be an excellent functional food to cover specific dietary needs for people with various ailments. This is due to the capability of the technology to modify the profile of essential amino acids and fats and to be enriched in vitamins, minerals, and bioactive compounds. However, there are various technical questions associated with growing and processing cultured meat. For example, grown cell sheets of cultured meat should be removed from a substrate without damaging the structure of the meat and/or the substrate.

Large-scale cell growth for edible meat production faces particular challenges. Other conventional apparatuses that are designed for the growth of adherent cells are limited in size and incorporate tortuous fluid flow paths to accommodate their size constraints. To grow cultured meat of sufficient physical dimensions (e.g., cell sheets), the growth of one or more cell sheets may require sufficient time where the cells remain adhered to a substrate for a predetermined time period (e.g., growth period). One or more fluids (e.g., growth media, culture media, liquid) may flow through the apparatus in a predetermined flow pattern to perfuse the cells and promote cell growth, differentiation, or adherence on one or more substrates. However, providing a predetermined fluid flow over large surface areas is challenging.

Once the cells are grown (e.g., production of a meat product) on a substrate, the grown meat product needs to be harvested (e.g., removed from the substrate) in a substantially intact manner for further processing. In some embodiments, recovery of one or more cell sheets is aided by a fluidic release mechanism (e.g., fluid-based shear stress), thereby allowing controlled and scalable production and collection of an edible meat product. In some embodiments, a fluid other than the one used for the growth of the cells may be used to separate a produced cell sheet from the substrate as an end product for collection. For example, a system for cell sheet growth may be configured to receive and distribute another fluid to one or more substrates in a predetermined flow pattern sufficient to separate the grown meat product from the substrates. Thus, systems and methods described herein provide significant improvements to conventional systems and techniques for growing cell sheets over substrates and for harvesting cell sheets.

SUMMARY

Disclosed embodiments provide an assembly and a system for delivering a fluid using a fluid dispenser.

Consistent with a disclosed embodiment, an assembly for delivering a fluid includes a fluid dispenser connected to a fluid supply conduit. The fluid dispenser includes a fluid outlet positioned along a length of the fluid dispenser. The fluid dispenser is configured to deliver the fluid from the fluid supply conduit at a flow rate that varies along the length of the fluid dispenser.

Consistent with another disclosed embodiment, a system including an enclosure is provided. Further, the system includes a plurality of substrates disposed within the enclosure and having vertical surfaces spaced apart from each other. The system also includes a fluid supply conduit configured to supply a fluid and a fluid dispenser disposed within the enclosure and connected to the fluid supply conduit. The fluid dispenser includes a fluid outlet positioned along a length of the fluid dispenser and configured to discharge the fluid at a flow rate that varies along the length of the fluid dispenser.

The foregoing general description and the following detailed description are exemplary and explanatory only and are not restrictive of the claims.

BRIEF DESCRIPTION OF THE DRAWINGS

The accompanying drawings are not necessarily to scale or exhaustive. Instead, the emphasis is generally placed upon illustrating the principles of the embodiments described herein. These drawings, which are incorporated in and constitute a part of this specification, illustrate several embodiments consistent with the disclosure, and, together with the detailed description, serve to explain the principles of the disclosure. In the drawings.

DETAILED DESCRIPTION

Reference will now be made in detail to exemplary embodiments discussed with regard to the accompanying drawings. In some instances, the same reference numbers will be used throughout the drawings and the following description to refer to the same or like parts. Unless otherwise defined, technical and/or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Figure 1A:
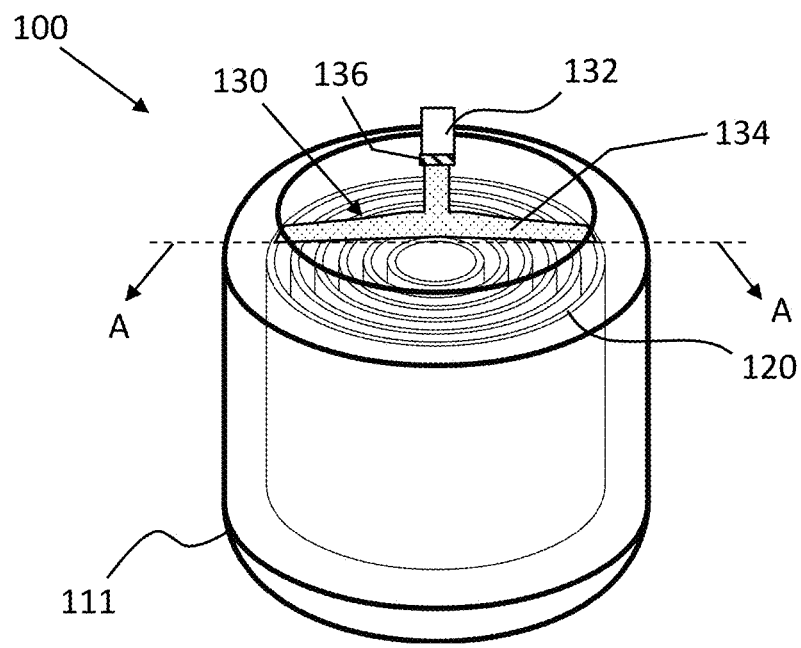
FIGS. 1A and 1B show an example system for facilitating cultured cell growth on one or more substrates, consistent with disclosed embodiments.

Consistent with disclosed embodiments, FIG. 1A illustrates an exemplary system 100 for growing cell sheets. In one exemplary embodiment, system 100 may be used for growing cells of cultured meat. System 100 may include an enclosure 111 (e.g., chamber, housing, container) defining a cavity and substrates 120 configured to grow cells. Further, system 100 may include a collector 118, as shown in FIG. 1B, located adjacent to a bottom portion of enclosure 111.

The components of system 100 (e.g., enclosure 111, substrates 120, collector 118) may be composed of a material including, but not limited to, one or more of polystyrene, polycarbonate, polychlorotrifluoroethylene, polyetherimide, polysulfone, polypropylene, silicone, polyetheretherketone, polymethylmethacrylate, nylon, acrylic, polyvinylchloride, vinyl, phenolic resin, petroleum-derived polymers, glass, polyethylene, terephthalate, stainless steel, titanium, aluminum, cobalt-chromium, chrome, silicates, glass, alloys, ceramics, carbohydrate polymer, mineraloid matter, and combinations or composites thereof. In some cases, the material comprising one or more components of system 100 may include multiple layers. For example, a component of system 100 may include a coating (e.g., a fluoropolymer coating, such as EPFE, ETFE, and the like, or antimicrobial coating (e.g., coating containing $TiO_2$ particles, copper particles, and the like).

In various embodiments, enclosure 111 may be configured to provide a sealed chamber to allow for the sterile growth of a product. Enclosure 111 may comprise one or more inlets configured to receive fluid and one or more outlets configured to allow the fluid to exit from enclosure 111. In some embodiments, the one or more inlets may be disposed on a first side of the enclosure, and the one or more outlets may be disposed on a second side of the enclosure, opposite the first side of the enclosure, as further discussed herein. Enclosure 111 may be of any suitable size and shape and capable of maintaining a target humidity and temperature environment required for cell growth. For example, enclosure 111 may be designed to be sufficiently thermally insulating for maintaining a target temperature within enclosure 111. In an example embodiment, enclosure 111 may have several walls separated by gaps or recesses (e.g., gaps or recesses may be partly evacuated or filled with gas) to achieve required thermal insulation. Other methods for providing the thermal insulation to enclosure 111 are also contemplated (e.g., a thermally insulating layer placed over enclosure 111).

Figure 1B:
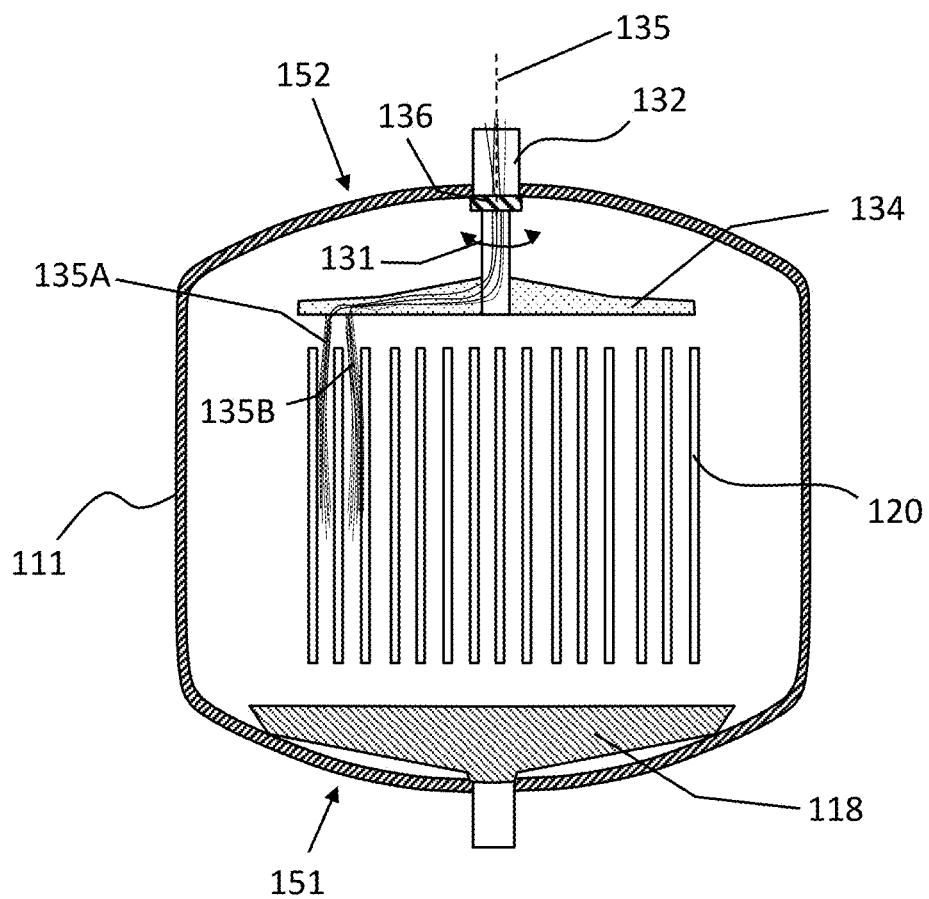

FIG. 1A shows an isometric view of system 100, and FIG. 1B shows a cross-sectional view of system 100 in plane A, as indicated in FIG. 1A. In an example embodiment, substrates 120 may be configured to have a cylindrical shape, and multiple concentric substrates may be used. In alternative embodiments, substrates 120 may be of any other suitable shape (e.g., planes, curved surfaces, spirals, such as Archimedean spiral, and the like). For example, substrates 120 may have lateral surfaces extending from an adjacent bottom end 151 of enclosure 111 towards a top end 151 of enclosure 111 and may be spaced apart from each other. Enclosure 111 may be partially or fully filled with fluid. When enclosure 111 is partially filled with fluid, an air-filled or gas-filled space may be present in enclosure 111 adjacent to top end 152.

Substrates 120 may allow for high-density growth of cells. For example, substrates 120 may comprise one or more surfaces configured to promote the adhesion, differentiation, and/or growth of cells to form a comestible product. Once grown to a predetermined size, the grown product may be separated from its respective substrate as described in more detail herein. The substrates of the disclosure can be of any predetermined size or shape. Further, substrates 120 may include roughness, waviness, and/or may be angled to a vertical direction (at least in some regions). It is also contemplated that the substrates may have other textures, for example, dimpled, slotted, etc. Substrates 120 may be composed of solid material and/or semi-solid material (e.g., hydrogel) or may include a mesh. In some embodiments, substrates 120 may comprise textured surfaces to promote the adhesion, differentiation, and growth of the cells/cell sheets. In some embodiments, substrates 120 may be manipulated to enhance one or more characteristics (e.g., coated to improve adhesion).

Substrates 120 may support the growth and retention of cells, including, but not limited to, cells comprising one or more of endoderm, mesoderm, ectoderm, and combinations thereof. Returning to FIGS. 1A and 1B, system 100 may include an assembly 130 for delivering a fluid to substrates 120. Assembly 130 may include a fluid dispenser 134 that may be connected to a fluid supply conduit 132. One or more filters may be disposed in or inline with fluid supply conduit 132 and may be configured to trap particulate matter to prevent such materials from clogging fluid dispenser 134. In one exemplary embodiment as illustrated in FIG. 1, fluid dispenser 134 may take the form of an elongated arm. For example, fluid dispenser 134 may be a radially extending arm configured to receive fluid from fluid supply conduit 132 and dispense fluid into enclosure 111. It is contemplated, however, that fluid dispenser 134 may take any of a variety of other shapes (e.g., circular, semi-circular, curvilinear, tubular, or other types of shapes). By way of example, in some embodiments, fluid dispenser 134 may have an "S"

shape with the rotational axis 135 located at a center of the S shape. In an example embodiment, fluid dispenser 134 may be configured to rotate in a plane generally perpendicular to an axis 135 of rotatable connection 136, as shown in FIG. 1B by arrow 131. Fluid dispenser 134 may be configured to dispense various fluids, as well as a growth media towards surfaces of substrates 120 while rotating in a circular path. In an example embodiment, fluid dispenser 134 may be used for providing nutrients to tissues (e.g., cell sheets grown on substrates 120), cleaning substrates 120, removing cell mass (e.g., harvesting cell culture) from substrates 120, delivering cells to substrates 120, sterilizing substrates 120 or some combination thereof.

FIG. 1B shows example fluid jets 135A-135B dispensed by fluid dispenser 134 from one or more fluid outlets positioned along a length of fluid dispenser 134 and configured to discharge a fluid received from fluid supply conduit 132. In an example embodiment, jets 135A-135B may be configured to deliver fluid in spaces between substrates 120 and towards surfaces of substrates 120.

Consistent with one embodiment of the present disclosure, fluid dispenser 134 may be configured to receive fluid and provide a predetermined fluid flow to one or more of substrates 120. For example, fluid dispenser 134 may be configured to receive and distribute the fluid to a plurality of substrates in a predetermined fluid flow pattern (e.g., using a substantially uniform and laminar flow to promote consistent cell growth across the surface of one or more of substrates 120). It is contemplated that fluid dispenser 134 may be configured to provide any number of different fluid flow patterns (e.g., laminar, transitional, turbulent, pressurized, variable, or a mix of these flow regimes). In some embodiments, the fluid flow through the fluid dispenser 134 may be assisted by gravity. In other embodiments, the fluid flow through fluid dispenser 134 may be driven by an external source, for example, a pump. In some exemplary embodiments, fluid dispenser 134 may be partially or fully submerged within fluid contained in enclosure 111. It is also contemplated that in some exemplary embodiments, fluid dispenser 134 may be disposed in the air or gas filled space above the fluid contained in enclosure 111.

Figures 2A, 2B:
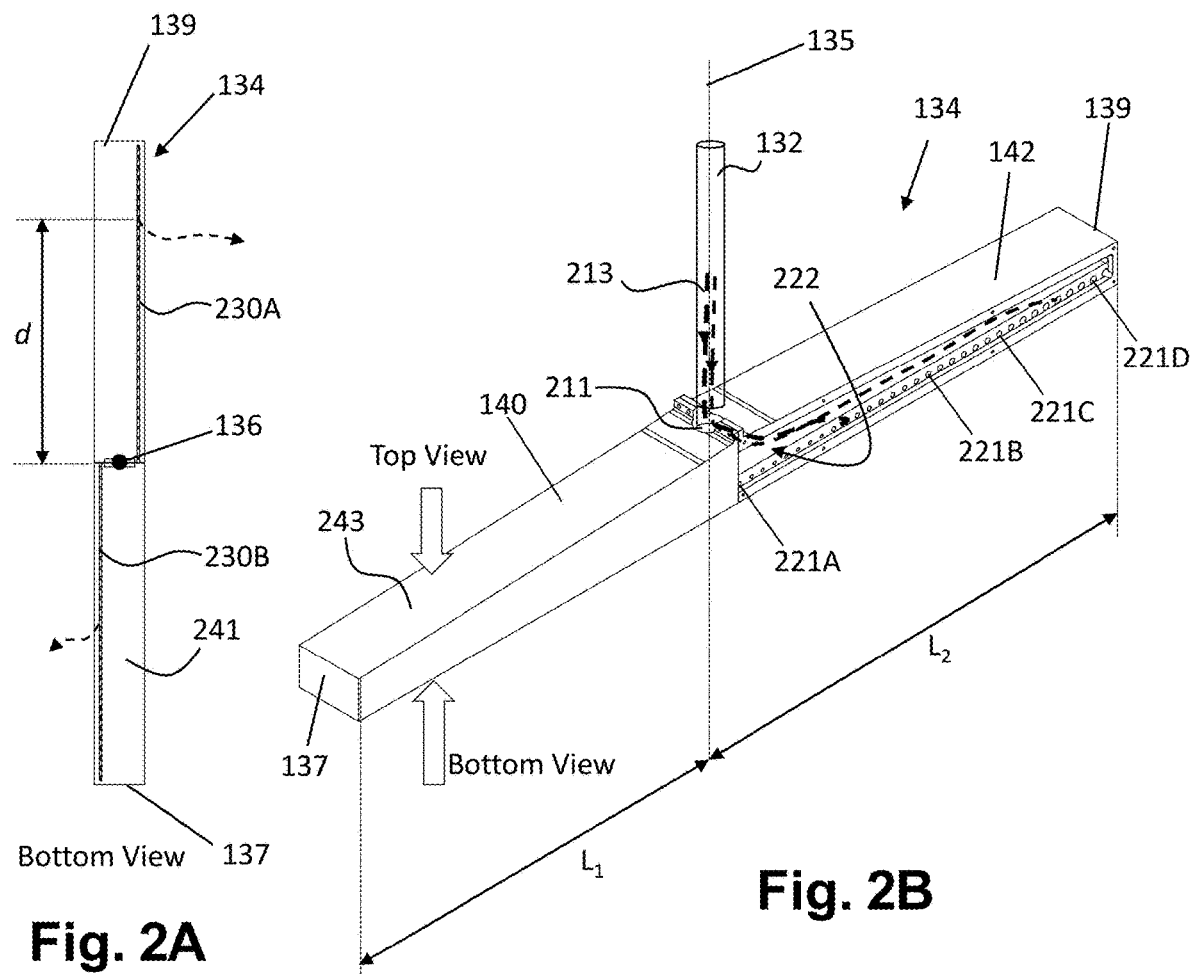
FIGS. 2A, 2B, and 2C show examples of fluid dispensers for delivering fluid to substrates for seeding, growing, and/or harvesting cultured cell sheets, consistent with disclosed embodiments.

Consistent with disclosed embodiments, fluid dispenser 134, as shown in FIGS. 2A and 2B, may have an elongated structure extending from axis 135. As illustrated in FIGS. 2A and 2B, fluid dispenser 134 may include arm 140 extending radially from axis 135 to distal end 137 and arm 142 extending radially from axis 135 to distal end 139. Arms 140 and 142 may extend over a part of or all of a diameter of enclosure 111. It is contemplated, however, that in some exemplary embodiments, fluid dispenser 134 may include only one of arms 140 or 142. Arm 140 may have a length $L_1$ and arm 142 may have a length $L_2$. Lengths $L_1$ and $L_2$ may be equal or unequal. In one example, arms 140 and 142 may extend in diametrically opposite sides. It is contemplated, however, that arms 140 and 142 may be disposed inclined relative to each other at any desired angle. It is also contemplated that in some example embodiments, fluid dispenser 134 may have more than or less than the two arms 140, 142 disposed at various angles relative to each other. In one example, the fluid dispenser may include an opening along the length of the fluid dispenser. For example, each of arms 140 and 142 may include an opening along the length of arms 140 and 142, respectively. In relation to the length of the fluid dispenser, the opening may be equally long, half as long, a quarter of the length, an eighth of the length, or some intermediate length thereof.

Fluid dispenser 134 may include one or more openings 211 for connecting with fluid supply conduit 132. Fluid dispenser 134 may also include one or more cavities 222 configured to receive fluid from fluid supply conduit 132. A flow of fluid, shown schematically by flow lines 213 in FIG. 2B, may be configured to pass through fluid supply conduit 132 into cavity 222. In an example embodiment, cavity 222 may be connected to a set of channels (e.g., channels 221A-221D, as shown in FIG. 2B). Although only four channels 221A-221D are illustrated in FIG. 2B, it is contemplated that cavity 222 may include any number of channels. The set of channels may be configured to carry fluid towards one or more outlets 230A and 230B located at the bottom portion of fluid dispenser 134, as shown in FIG. 2A. In an example embodiment, outlets 230A and 230B may comprise openings positioned along a length $L_1$ or $L_2$ of fluid dispenser 134. In one exemplary embodiment, length $L_1$ or $L_2$ of fluid dispenser 134 may be measured from a center point of arm 134 to an end point 137 of fluid dispenser 134, as shown in FIGS. 2A-2B.

In an example embodiment, fluid dispenser 134 may be configured to deliver a fluid from fluid supply conduit 132 to fluid outlets 230A and 230B. In one exemplary embodiment, a flow rate of the fluid being discharged from a particular location along a fluid outlet may be substantially proportional to a distance d of that location from axis 135. It is contemplated, however, that the flow rate may be uniform or non-uniform at different fluid outlets regardless of their distance from axis 135. It is also contemplated that the flow rate may be varied in numerous ways along a length (or radius) of fluid dispenser 134.

In example embodiments, outlets 230A and 230B may be located at a bottom surface 241 of fluid dispenser 134 and may form elongated openings, as shown in FIG. 2A. In some cases, bottom surface 241 may be symmetric about a central line of symmetry (e.g., a radial axis extending from axis 135). That is, bottom surface 241 may have a generally equal width on either side of the radial axis. It is contemplated, however, that in other exemplary embodiments, bottom surface 241 may be asymmetrically disposed relative to the central line of symmetry, having different widths on opposite sides of the radial axis. It is further contemplated that in some exemplary embodiments, bottom surface 241 may extend to different widths relative to the radial axis at different radial distances from axis 135. As shown, outlet 230A may be located on one side of fluid dispenser 134 (e.g., at a right side of the central line of symmetry), and outlet 230B may be located on an opposite side of fluid dispenser 134 (e.g., at a left side of the central line of symmetry). In some cases, more than two outlets 230A and 230B may be used.

Figure 2C:
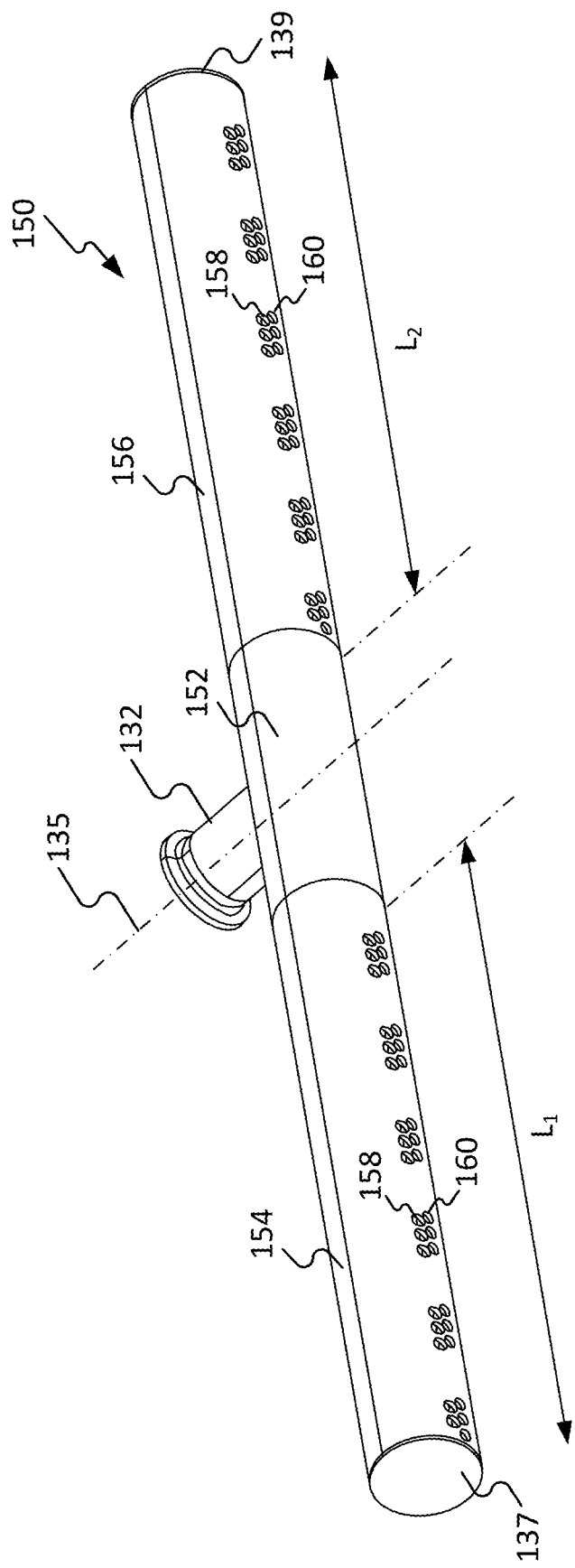

FIG. 2C illustrates an exemplary embodiment of fluid dispenser 150. Consistent with disclosed embodiments, fluid dispenser 150, as shown in FIG. 2C, may have an elongated structure extending from axis 135. As illustrated in FIG. 2C, fluid dispenser 150 may include arms 154 and 156 that may be connected to conduit 132 via connector 152. In one exemplary embodiment as illustrated in FIG. 2C, connector 152 may be a T-shaped connector, although other shapes (e.g., Y-shape, etc.) are also contemplated. Arm 154 may extend from connector 152 to distal end 137 and arm 146 may extend from connector 152 to distal end 139. Arms 154 and 156 may each extend over a part of or all of a diameter of enclosure 111. It is contemplated, however, that in some exemplary embodiments, fluid dispenser 134 may include only one of arms 154 or 156. Arm 154 may have a length $L_1$ and arm 156 may have a length $L_2$ as measured radially from axis 135. Lengths $L_1$ and $L_2$ may be equal or unequal. Similarly, connector 152 may extend on either side of axis 135 to equal or unequal lengths. In one example, arms 154 and 156 may extend in diametrically opposite directions. It is contemplated, however, that arms 154 and 156 may be disposed inclined relative to each other at any desired angle. It is also contemplated that in some example embodiments, fluid dispenser 150 may have more than or less than the two arms 154, 156 disposed at various angles relative to each other.

In one exemplary embodiment as illustrated in FIG. 2C, arms 154 and 156 may have a generally cylindrical shape with a generally cylindrical hollow interior. It is contemplated, however, that both the outer and interior shapes may have various other shapes (e.g., elliptical, rectangular, square, or any other shape). In one example, the interior volume of an arm may decrease linearly as a function distance from connector 152 to manipulate pressure and flow rate along an arm. Arms 154 and 156 may include openings 158 and 160. Openings 158 and 160 may be through holes that may extend through the thickness of a wall of arms 154 and 156. Openings 158 and 160 may have a circular cross-section, although other shapes (e.g., elliptical, polygonal, etc.) of openings 158 and 160 are also contemplated. Openings 158 and 160 may have a generally cylindrical shape. It is contemplated however that openings 158 and 160 may have a cross-sectional area that may vary over a thickness of the wall of arms 154 and 156.

In one exemplary embodiment as illustrated in FIG. 2C, arms 154 and 156 may be disposed adjacent to each other. Openings 158 and 160 may be formed in groups of 3 openings with the groups separated from each other radially at equal or unequal radial distances. It is to be understood that each group of openings may include more than or less than 3 openings. Each group of openings 158 may be radially aligned (e.g., overlapping with) or offset relative to a corresponding set of openings 160. It is contemplated that in some exemplary embodiments, openings 158 and 160 may be formed along the lengths of arms 154 and 156 in any other desired pattern. Each opening may have its diameter increased or decreased to further control flow rate at each point along an arm.

It is contemplated that fluid dispenser 134 and/or 150 may be manufactured using various manufacturing methods, including without limitation, machining, welding, brazing, flanging, printing, molding, etc. In some exemplary embodiments, fluid dispenser 134 and/or 150 may be made of stainless steel, although other materials are also contemplated. It is further contemplated that fluid dispenser 134 and/or 150 may dispense one or more of coating material, media, cell culture, cleaning detergents (e.g., water, acid, caustic, disinfection agents, enzymatic cleaners, etc.), steam, wash-buffer, and/or other types of liquids or gases into enclosure 111. One or more of these exemplary materials may be dispensed by fluid dispenser 134 and/or 150 when fluid dispensers 134, 150 are partially or fully submerged or positioned in the air or gas filled portion of enclosure 111. In some exemplary embodiments, fluid dispenser 134 and/or 150 may also be configured to introduce gases such as air, carbon dioxide, oxygen, nitrogen, etc., into enclosure 111. It will be understood that when fluid dispenser 134 and/or 150 are configured to introduce gases while being submerged in the fluid contained within enclosure 111, fluid dispenser 134 and/or 150 may act like a sparger. In some exemplary embodiments, an operating pressure of fluid in fluid dispenser 134 and/or 150 may range between 2 to 10 bars, although other operating pressures are also contemplated.

Although fluid dispenser 134 has been illustrated and described as being positioned adjacent to the top end 152 of enclosure 111, the present disclosure is not so limited. It is contemplated that in some exemplary embodiments, fluid dispenser 134 and/or 150 may be located on a side wall of enclosure 111. In yet other exemplary embodiments, fluid dispenser 134 and/or may be positioned adjacent bottom end 151 and may be configured to direct fluid flow upward toward substrates 120. In some exemplary embodiments, fluid dispenser 134 and/or 150 may be disposed at an intermediate height between top end 152 and bottom end 151, for example, with substrates 120 having two sections separated from each other by a vertical gap to accommodate fluid dispenser 134 and/or 150. Positioning fluid dispenser 134 and/or 150 at an intermediate height may help improve the washing or harvesting efficiency of the culture on substrates 120 or may help to wash the walls of enclosure 111. It is also contemplated that in some exemplary embodiments, fluid dispenser 134 and/or 150 may include extension arms extending from distal ends 137 of, for example, arms 140 or 154, respectively, towards bottom end 151 of enclosure 111. These extension arms may help dispense fluid at intermediate heights between top end 152 and bottom end 151 of enclosure 111.

Figure 3A:
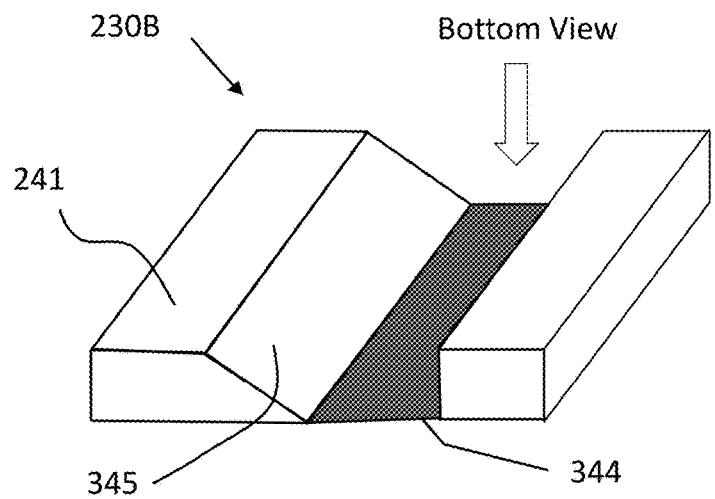
FIG. 3A shows a shape of an example outlet region for a fluid dispenser, consistent with disclosed embodiments.

Returning to dispenser 134 illustrated in FIGS. 2A and 2B, an exemplary embodiment of an outlet (e.g., outlet 230B) is illustrated in FIG. 3A. As illustrated in FIG. 3A, the outlet (e.g., outlet 230B) may have a selected side cross-sectional shape 344 that may include a slanted side 345. Cross-sectional shape 344 is only illustrative, and other shapes with slanted or curved sides may be used.

In example embodiments, outlets 230A and 230B may be openings with a cross-sectional shape of the openings having four sides (e.g., outlets 230A and/or 230B may be rectangles). Alternatively, outlets 230A and/or 230B may have trapezoidal shapes). For example, in some embodiments, a width of outlets 230A, 230B may be smaller adjacent to axis 135 and larger adjacent to distal end 137 or vice versa. In some embodiments, a fluid outlet (e.g., outlet 230B) may have a trapezoidal shape having a first side and a second side opposite to the first side, wherein the first side is proximate to a center of fluid dispenser 134 and the second side is proximate to distal end 408 of fluid dispenser 134. In an example embodiment, the second side of fluid outlet 230B may be larger than the first side.

Figure 3B:
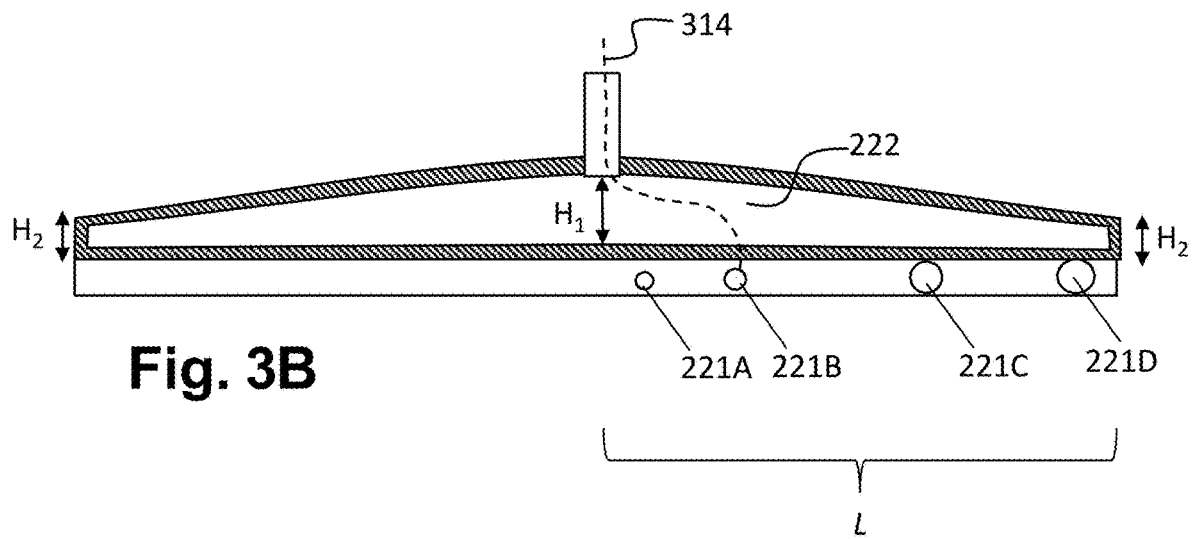
FIG. 3B shows an example cross-sectional shape of a cavity within a fluid dispenser, consistent with disclosed embodiments.

In various embodiments, cavity 222 may be configured to direct fluid from conduit 132 to channels 221A-221D and, subsequently, to outlets 230A and 230B. Cavity 222 may be of any suitable shape. In an example embodiment, a cross-sectional view of cavity 222 is shown in FIG. 3B. Cavity 222 may be configured to be wider at a middle region (e.g., adjacent to axis 135) and narrower at the sides (e.g., adjacent to distal end 137). For example, at the middle region, cavity 222 may have a height $H_1$ that is larger than the height $H_2$ at the ends of cavity 222. In various embodiments, the external shape of fluid dispenser 134 may substantially conform to the shape of cavity 222. In an example embodiment, cavity 222 may form a three-dimensional shape. In some cases, cavity 222 may have one or more planes of symmetry. In an example embodiment, a height of cavity 222 (herein, also referred to as a baffle) may decrease along the length of the fluid dispenser.

Figure 3C:
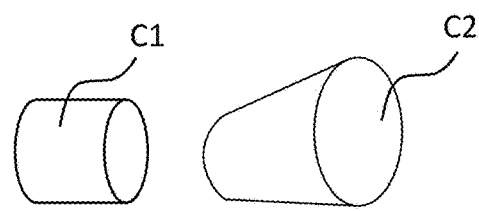
FIG. 3C shows examples of channel shapes, consistent with disclosed embodiments.

As indicated by flow line 314, cavity 222 may be connected to a set of channels (e.g., channels 221A-221D) configured to transmit fluid from cavity 222 to fluid outlets 230A or 230B. Any suitable number of channels may be used. Further channels 221A-221D may be of variable size and may be distributed along a length L of fluid dispenser 134 in a selected way. In an example embodiment, channels 221A-221D may have any suitable three-dimensional shape. For example, a channel shape may be a cylinder C1 or a truncated cone C2, as schematically shown in FIG. 3C.

Figure 4A:
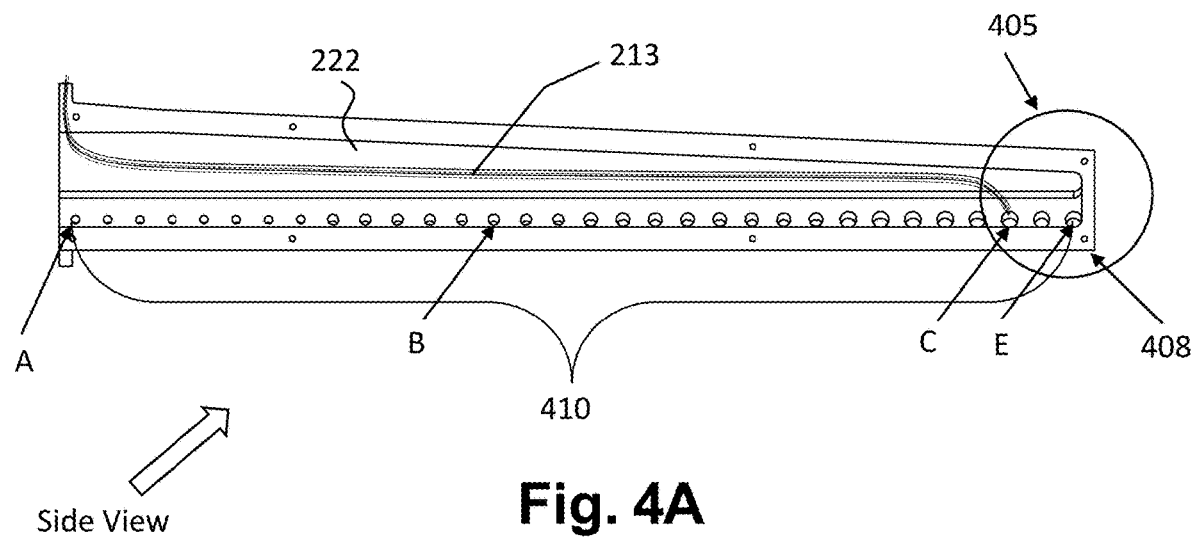
FIGS. 4A and 4B show additional features of a fluid dispenser for delivering fluid to substrates for growing and/or harvesting cultured cell sheets, consistent with disclosed embodiments.
Figure 4B:
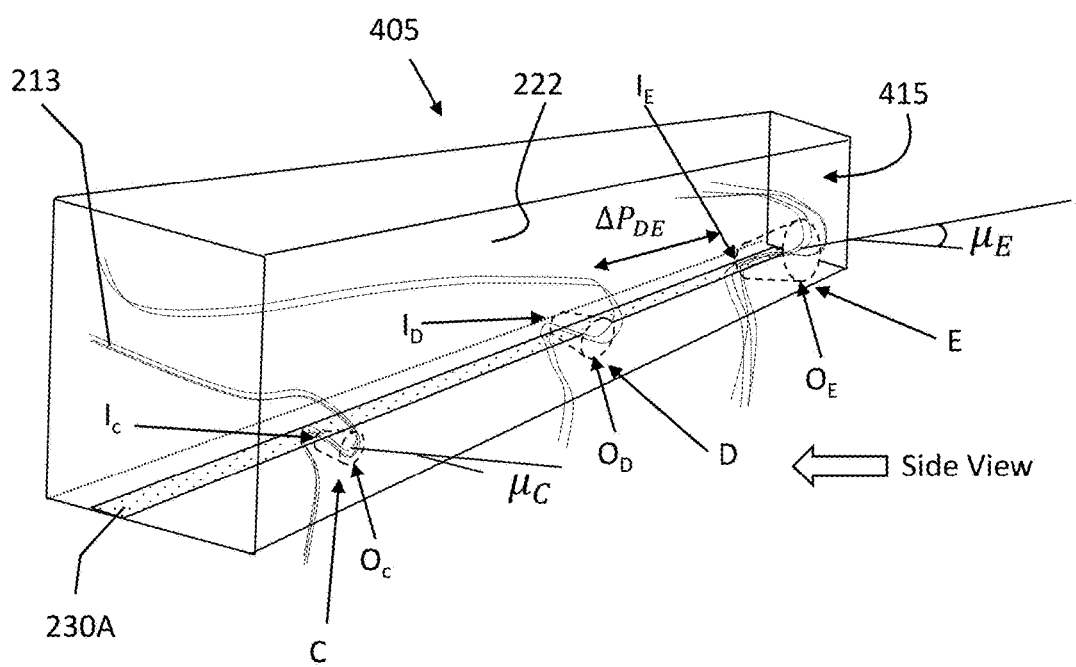

FIG. 4A illustrates a portion of fluid dispenser 134 that includes a cavity 222 for carrying fluid as well as channels 410. In some embodiments, channels 410 may include narrow channels (e.g., channel A) and wide channels (e.g., channel E). A narrow channel A may have a smaller dimension (e.g., diameter, width, inner volume, etc.) relative to a wide channel E. FIG. 4B illustrates an isometric view of a portion of fluid dispenser 134 indicated by region 405. Channels 410 may be configured to receive fluid indicated by flow lines 213, as shown in FIG. 4A, and may carry the fluid towards a fluid outlet (e.g., fluid outlet 230A, as shown in FIG. 4B). As shown in FIG. 4B, channel D may be wider than channel C, thus allowing for a larger amount of fluid flow (e.g., larger volume flow rate). In some embodiments, channels 410 may be spaced uniformly along length L of fluid dispenser 134, and in other embodiments, channels 410 may be spaced non-uniformly. In an example embodiment, more channels may be present at a distal end 408 (shown in FIG. 4A) than at a central portion of fluid dispenser 134. Alternatively, channels 410 may be distributed along fluid dispenser 134 in any other suitable way.

In various embodiments, channels 410, such as channels A-E, may be of any suitable shape, size, and orientation. For example, channels A-E may have a cylindrical shape, tapered cylindrical shape, and the like. Cross-sections of channels 410 may be of any suitable shape (e.g., circular, elliptical, rectangular, triangular, and the like). In some cases, the cross-sectional shape (or cross-sectional size) of channels 410 may change along the lengths of those channels. Such changes in shape or size of a channel along the length of the channel may promote mixing of the flow within the channel. It is also contemplated that different channels 410 disposed along a length of fluid dispenser 134 may have different cross-sectional shapes and/or sizes. In some exemplary embodiments, fluid-contacting surfaces of channels 410 may be textured to alter the fluid flow regimes and further promote mixing of the flow within channels 410.

As shown in FIG. 4B, channels C-E may include respective inlets $I_C$, $I_D$ and $I_E$ (e.g., inflow regions into which fluid is entering the channels) and outlets $O_C$, $O_D$, and $O_E$ (e.g., outflow regions from which the fluid is exiting the channels). Channel sizes (including inlet and outlet areas) may be configured such that a distribution of channel resistance to flow of fluid decreases towards a distal end (i.e., end 408, as shown in FIG. 4A) of fluid dispenser 134. In some embodiments, sizes of the channels may be configured to increase towards distal end 408 of fluid dispenser 134, although other variations of channel sizes are also contemplated. Although only three channels C, D, and E are illustrated in FIG. 4B, it is contemplated that fluid dispenser 134 may include any number of channels.

In various embodiments, channels may have any suitable orientation. For example, an axis of channel E may be oriented at an angle $\mu_E$ with respect to a normal direction of surface 415 of fluid dispenser 134. Other channels may be oriented at different angles. For example, channel C may be oriented at an angle $\mu_C$ which may be smaller than, larger than, or equal to $\mu_E$. Such differences in orientation may result in different flow rates between channels C and E. Additionally, or alternatively, the differences in the flow rates for channels C and E (or any other channel from among channels 410) may be affected by a channel's cross-sectional size, shape, obstructions that may be present within the channel, or surface properties of the channel (e.g., surface properties may be influenced by a roughness within the channel, a material forming the channel, and the like). It is also contemplated that one or more of channels C, D, and/or E, 221A-D, and/or openings 158, 160 of fluid dispenser 150 may be oriented such that fluid exiting one or more of these channels may be directed at various desired angles onto one or more side walls of enclosure 111. Doing so may help ensure improved cleaning of enclosure 111 or improved homogenization of the fluid within enclosure 111.

In various embodiments, a flow rate through a channel (e.g., channel E) may depend on a pressure difference across channel E (i.e., a pressure difference between the inlet of channel E and the outlet of channel E), as well as a cross-sectional area of channel E. For example, for a given cross-sectional area, the larger the pressure difference across channel E, the higher is the flow rate. Note that the pressure difference across channel E may be a function of a pressure difference across channel D due to a possible pressure drop $\Delta P_{DE}$ between channel D and channel E. In some cases, pressure drop, such as $\Delta P_{DE}$ may be controlled via obstructions presented in cavity 222, as further described below.

Figure 5:
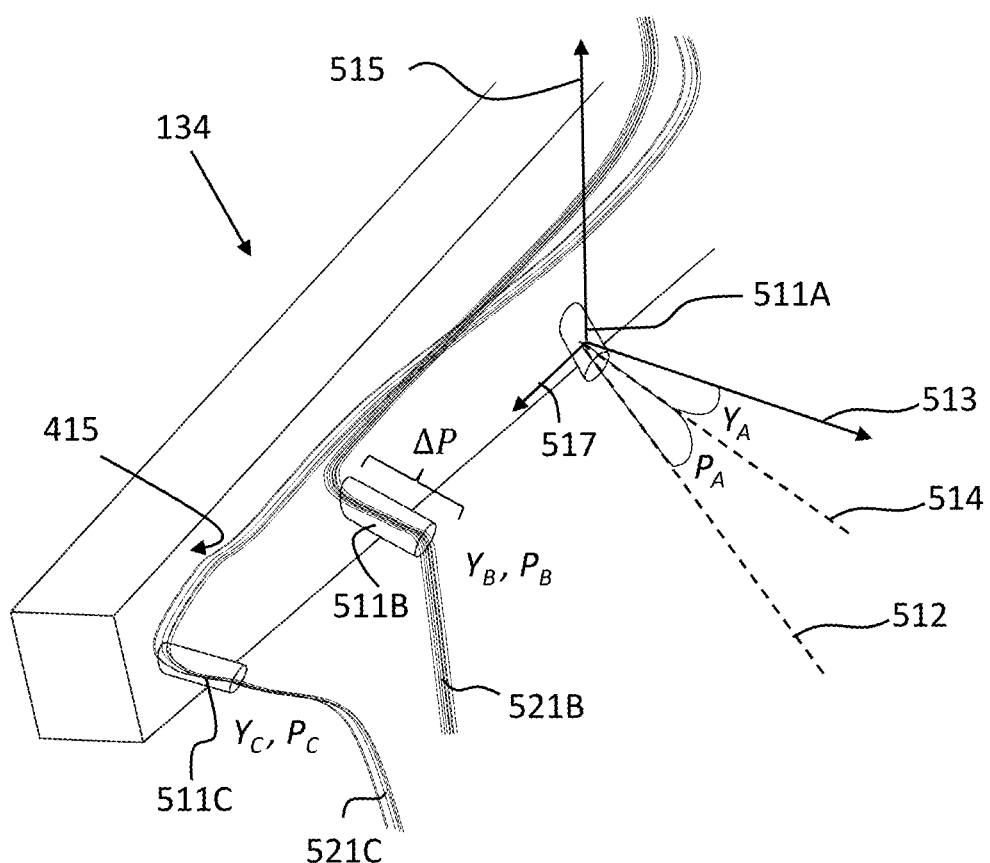
FIG. 5 shows a fluid dispenser having nozzles, consistent with disclosed embodiments.

It should be appreciated that fluid outlets 230A and 230B are only illustrative, and other types of outlets may be used. In an example embodiment, fluid outlets 230A and 230B may have a varying width as a function of length L. For instance, in one exemplary embodiment, a width of outlets 230A and 230B may be narrower adjacent to rotational axis 135 and may increase towards distal end 408 of fluid dispenser 134. Although outlets 230A and 230B have been illustrated as extending through a length of fluid dispenser 134, alternatively, a plurality of localized outlets spaced apart from each other along the length of fluid dispenser 134 are also contemplated. For example, FIG. 5 illustrates an example embodiment having protruding elements (e.g., nozzles 511A-511C). Each nozzle may be of a suitable size and shape (e.g., may have a suitable cross-sectional area, as described above, in relation to channels 410). Some or all of nozzles 511A-511C may have a uniform or non-uniform cross-sectional area. Further, each nozzle may have particular orientation angles characterized, for example, by a yaw angle Y and a pitch angle P. In an example embodiment, a yaw angle $Y_A$ may be a rotational angle obtained by rotating nozzle 511A around axis 515, which may be a tangent to face 415 and may be perpendicular to a direction 513 normal to face 415. Yaw angle $Y_A$ results from rotating nozzle 511A around axis 515 away from direction 513, as shown in FIG. 5. Nozzle 511A may have a pitch angle $P_A$ which may be an angle of inclination between an axis 512 of nozzle 511A and direction 514, with rotation performed around direction 517 (direction 517 is a cross-product of directions 513 and 515). Similarly, nozzles 511B and 511C may have respective yaw angles $Y_B$ and $Y_C$ and respective pitch angles $P_B$ and $P_C$. In an example embodiment, fluid dispenser 134 may include mechanisms for orienting nozzles 511A-511C to determine a particular fluid flow pattern (herein, the fluid flow pattern is indicated by flow lines 521B and 521C) for delivering fluid to surfaces of substrates 120. For example, nozzles 511A-511C may be connected to a thrust vectoring system configured to orient nozzles using, for example, electrical motors, which enables control over numerous flow characteristics, such as flow rate, flow velocity, angular velocity, flow direction, flow angle, etc. It is also contemplated that in some exemplary embodiments, fluid outlets 230A, 230B and/or nozzles 511A-511C may be oriented such that fluid exiting one or more of these outlets or nozzles may be directed at various desired angles onto one or more side walls of enclosure 111. Doing so may help ensure improved cleaning of enclosure 111 or improved homogenization of the fluid within enclosure 111.

Further, the fluid flow pattern may be determined by a value of a pressure drop ΔP across a nozzle (e.g., nozzle 511B) and a cross-sectional area of the nozzle. For example, for a given cross-sectional area, for high-pressure drop values, nozzle 511B may emit high-velocity fluid jets, while for low-pressure drop values, nozzle 511B may emit low-velocity fluid jets.

Nozzles 511A-511C illustrate one possible embodiment of fluid outlets from fluid dispenser 134. Other types of outlets may include openings, nozzles with adjustable valves, and the like. For instance, valves may be used for each nozzle 511A-511C to adjust the flow rate for the respective nozzle. Additionally, or alternatively, as described above, one or more nozzles 511A-511C may include a thrust vectoring system for adjusting pitch and yaw angles of one or more nozzles. In an example embodiment, pitch and yaw angles for one or more nozzles may be selected based on the desired fluid flow rates and flow patterns for the one or more nozzles. It is also contemplated that in some exemplary embodiments, the pitch and yaw angles may be manually adjusted by manually rotating and orienting the one or more nozzles in any desired direction. It is also contemplated that in some exemplary embodiments, the one or more nozzles may be equipped with mechanical linkages or other devices to allow the pitch and yaw angles of the one or more nozzles to be changed automatically, for example, by an electronic controller. Although only three nozzles 511A-511C are illustrated in FIG. 5, it is contemplated that fluid dispenser 134 may include any number of nozzles, openings, or other types of outlets.

Figure 6A:
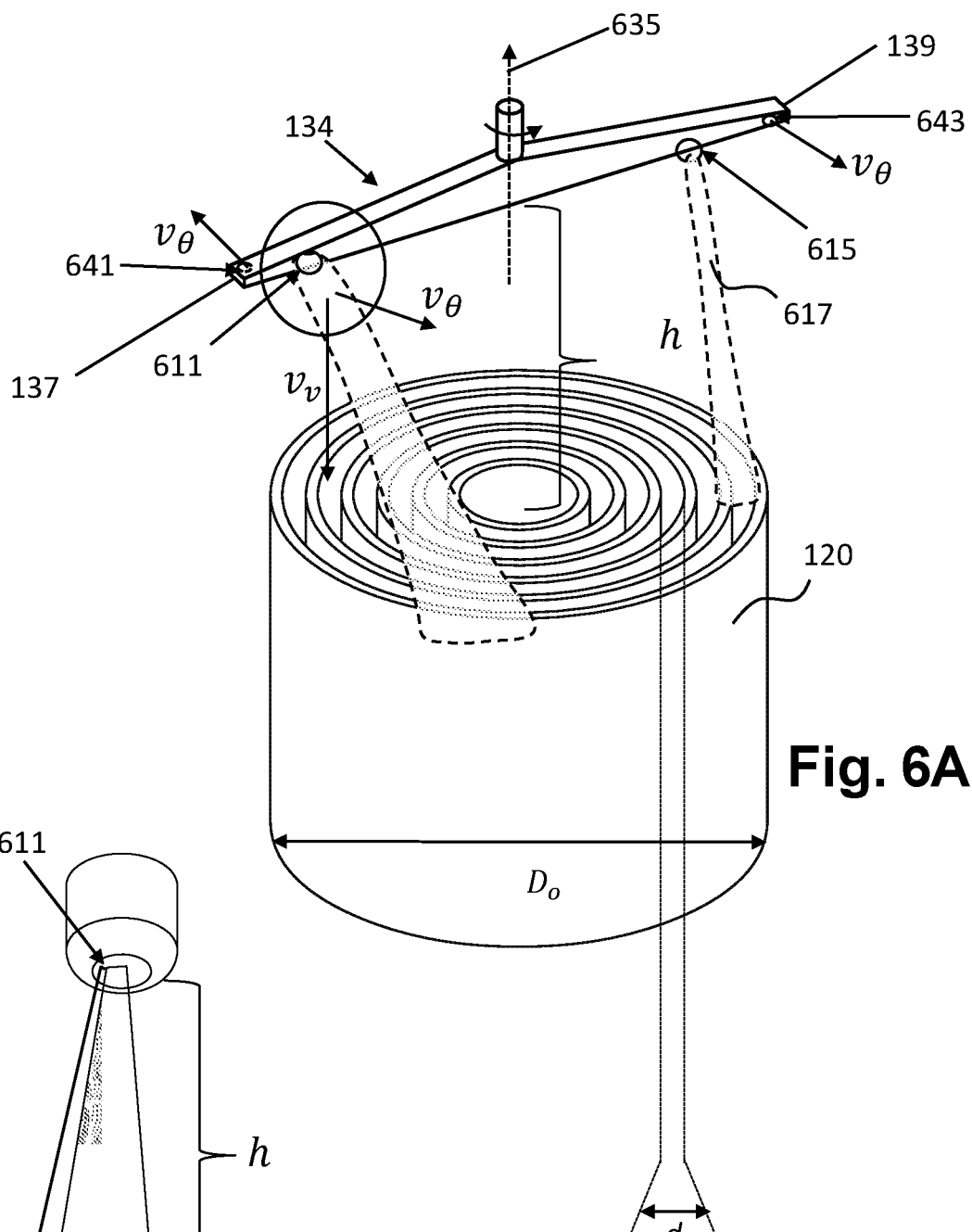
FIG. 6A shows an embodiment of an example system for facilitating cultured cell growth having the fluid dispenser, consistent with disclosed embodiments.

FIG. 6A shows fluid dispenser 134 positioned a distance h above substrates 120. A fluid outlet 611 may be configured to emit a fluid jet traveling towards substrates 120. In an example embodiment, a fluid element of the fluid jet may have a vertical velocity component $v_v$ and a velocity component $v_\theta$ perpendicular to a radial direction and in a plane of rotation of fluid dispenser 134. Velocity component $v_\theta$ is due to a rotation of fluid dispenser 134, as well as to a particular orientation of a channel carrying the fluid at fluid outlet 611 (e.g., if the channel at a fluid outlet is a nozzle, such as nozzle 511A, the orientation is defined by angles $Y_A$ and $P_A$, as shown in FIG. 5). In various embodiments, controlling the pressure of the fluid in fluid dispenser 134 may allow for controlling $v_v$ and $v_\theta$, while controlling the rotational speed of fluid dispenser 134, allows for controlling $v_\theta$.

In some exemplary embodiments, a rotation of fluid dispenser 134 may be performed by a suitable motor (e.g., an electric motor). In other exemplary embodiments, a rotation of fluid dispenser 134 may be facilitated by a magnetic force (e.g., fluid dispenser 134 may include a magnet located at one or more ends of fluid dispenser 134, which may be attracted to or repelled by electromagnets placed within or outside enclosure 111).

It should be appreciated that various approaches may be used to control the rotation of fluid dispenser 134. In an example approach, a controller may be used to control the direction and speed of fluid dispenser 134. The controller may include a computing device having a processor, a memory, one or more sensors for determining the position and angular velocity of fluid dispenser 134. The controller may also include instructions for determining a speed and direction of rotation of fluid dispenser 134 based on data obtained from the one or more sensors. The controller may also determine the commands for a motor that is configured to rotate fluid dispenser 134.

Additionally, or alternatively, the rotation of fluid dispenser 134 may be due to a fluid being ejected by fluid dispenser 134, such that the fluid has a velocity component. For instance, ejecting the fluid having velocity component $v_\theta$ results in a reactional force acting on fluid dispenser 134, which may cause fluid dispenser 134 to rotate in a direction opposite to a direction of velocity $v_\theta$ of the ejected fluid. In an example embodiment, when fluid dispenser 134 is rotated due to the fluid being ejected from one or more fluid outlets of the fluid dispenser 134 (e.g., fluid outlets 230A and 230B, as shown in FIG. 2A), rotation of fluid dispenser 134 may be controlled by controlling a flow rate of fluid flowing through fluid dispenser 134.

In some cases, fluid dispenser 134 may have a first outlet configured to eject fluid with a positive velocity $v_\theta$ (e.g., the positive velocity $v_\theta$ may be directed in a clockwise direction) and a second outlet configured to eject fluid with a negative velocity $v_\theta$ (e.g., the negative velocity ve may be directed in a counter-clockwise direction). Arranging the outlets to eject fluid with opposing velocities, may allow the controller to control a direction of rotation of fluid dispenser 134 more precisely. For example, the controller may be able to stop the fluid dispenser 134 from rotation by ejecting fluid from the two outlets at equal and opposite velocities. Alternatively, the controller may increase or decrease the magnitude of the velocity from one of the two outlets to cause fluid dispenser 134 to rotate at a desired rotational speed in a clockwise or counter-clockwise direction. For instance, FIG. 6A shows a fluid outlet 611 configured to deliver fluid such that a rotation in a clockwise direction is applied to fluid dispenser 134 (i.e., torque is directed as indicated by direction 635). Additionally, a fluid outlet 615 may be configured to deliver fluid 617 to substrates 120 such that a rotation in a counterclockwise direction is applied to fluid dispenser 134 (i.e., torque is directed in the direction negative to direction 635). A controller may be configured to control a flow rate of fluid exiting fluid outlets 611 and 613 to control a rate and/or direction of rotation of fluid dispenser 134. It is also contemplated that in some embodiments, the rate and/or direction of rotation of fluid dispenser 134 may be controlled by adjusting one or more valves that may control a flow rate of the fluid exiting, for example, fluid outlets 611 and/or 615. In some embodiments, the flow rates of the fluid exiting fluid outlets 611 and/or 615 may be adjusted to ensure that fluid dispenser 134 oscillates by first moving in one direction and then moving in an opposite direction. As also discussed above, in some exemplary embodiments, fluid outlets 611, 615 may be oriented such that fluid exiting one or more of these outlets or nozzles may be directed at various desired angles onto one or more side walls of enclosure 111. Doing so may help ensure improved cleaning of enclosure 111 or improved homogenization of the fluid within enclosure 111.

In some example embodiments, fluid dispenser 134 may include openings 641 and 643 configured to eject fluid to rotate fluid dispenser 134. For example, as illustrated in FIG. 6A, opening 641 may be located adjacent to distal end 137, whereas opening 643 may be located adjacent to distal end 139. Both openings 641 and 643 may be oriented so that fluid exiting openings 641 and 643 has a primary velocity component in the circumferential direction (e.g., $v_\theta$). For example, both openings 641 and 643 may be disposed on sides of fluid dispenser 134 that may be generally perpendicular or inclined relative to bottom surface 241 (see FIG.

2A). Thus, for example fluid exiting openings 641 and 643 may have minimal or near zero velocity component $v_y$. As illustrated in FIG. 6A, fluid exiting openings 641 and 643 may cause fluid dispenser 134 to rotate in a counter-clockwise direction. In these exemplary embodiments, openings 641 and 643 may be primarily responsible for causing fluid dispenser 134 to rotate about axis 635. It is contemplated that in some embodiments, fluid dispenser 134 may include additional openings disposed on an opposite side of dispenser 134 to allow fluid dispenser 134 to be rotated in a clockwise direction. Openings 641 and 643 and/or corresponding openings on an opposite side of fluid dispenser 134 may be manually or automatically opened or closed to control the rotational direction of fluid dispenser 134. It is also contemplated that one or both of openings 641 and 643 may be equipped with valves that may allow control of the fluid velocity exiting openings 641 and 643, respectively, and a direction of rotation of fluid dispenser 134 may be controlled by controlling the exit velocity of the fluid from openings 641 and 643. In embodiments of fluid dispenser 134 having openings such as 641 and 643, other openings such as 611 and 615 may be oriented such that fluid exiting these openings may be directed to impinge on substrates 120. In these exemplary embodiments, openings such as 611 and 615 may have a very small velocity component in the circumferential direction, which may or may not significantly contribute to rotation of fluid dispenser 134. Although openings 641 and 643 have been described with respect to fluid dispenser 134, similar openings may be provided on fluid dispenser 150.

It should be appreciated that fluid dispenser 134 may be configured to be rotated by combining the action of a motor as well as torques generated by fluid exiting from various positions at one or more fluid outlets. In an example embodiment, a controller may include processor instructions for performing operations that may include obtaining data from various sensors (e.g., sensors for determining a position of fluid dispenser 134, sensors for determining angular velocity of fluid dispenser 134, sensors for determining fluid pressure within fluid dispenser 134, sensors for determining volume flow rate at different positions at one or more fluid outlets, sensors for determining torques applied to fluid dispenser 134 due to a fluid released by fluid dispenser 134, or any other suitable sensors) and determining torques that may be produced by the motor to yield a target rotation rate for fluid dispenser 134. Additionally, or alternatively, the controller may modify torques exerted by the fluid released by fluid dispenser 134 to yield the target rotation rate for fluid dispenser 134.

Fluid dispenser 134 and/or 150 may be configured to rotate at a speed ranging between 1 and 120 rpm (revolutions per minute) when fluid dispensers 134, 150 are located in the air filled or gas filled portion of enclosure 111. It is to be understood that the rotational speed of fluid dispenser 134 and/or 150 when partially or fully submerged in the fluid in enclosure 111 may be smaller than when fluid dispenser 134 and/or 150 is not submerged in the fluid. It is also contemplated that one or more of the rotational techniques discussed above (e.g., directed fluid jets, motors, magnetic materials) may be used to rotate fluid dispensers 134, 150 continuously or discontinuously (e.g., in a pulsed manner, rotating for some time and stopping in between subsequent rotations).

Figure 6B:
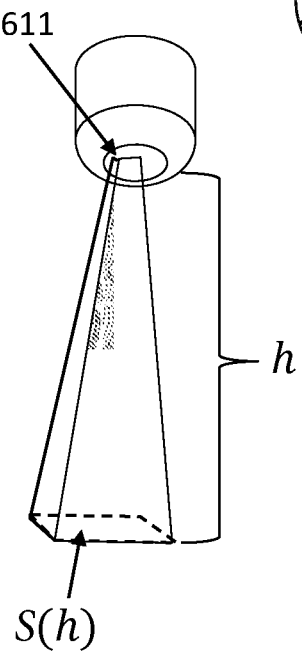
FIG. 6B shows an example fluid jet emitted by a fluid dispenser, consistent with disclosed embodiments.

FIG. 6B shows an example fluid jet emitted from a position 611. Herein, the term "jet" characterizes any type of flow of a fluid emitted from a region (otherwise referred to as a position) of fluid outlet. For example, as shown in FIG. 2A, such a region may be region 233. In some cases, fluid dispenser 134 may be configured to modify the cross-sectional area S(h) of the fluid jet at a distance h, as shown in FIG. 6B. For example, the cross-sectional area S may be modified by adjusting characteristics of a fluid outlet (e.g., by mechanically adjusting the fluid outlet exit area, fluid outlet exit shape, and the like). For instance, wide low-velocity fluid jets, herein referred to as mist jets, may be used for delivering nutrients to cell culture, while narrow high-velocity fluid jets, herein referred to as stream jets, may be used to remove cell culture from substrates 120 for harvesting the cell culture. In an example embodiment, wide fluid jets may have a characteristic cross-sectional size (herein, the characteristic cross-sectional size may be determined as a square root of area S) on a scale of a diameter Do of an outside substrate, as shown in FIG. 6A, while narrow jets may have a characteristic cross-sectional size on a scale d of a distance between two substrate walls, as shown in FIG. 6A. In alternative examples, the fluid jet may take on a flow pattern characterizable as a jet, soaker, angled, mist, centered, full, flat, shower, cone, and the like.

Additionally, or alternatively, the velocity of a fluid jet may be modified by modifying a pressure within fluid dispenser 134. For example, for supplying nutrients to cell culture, low-pressure values may be used, while for removing cell culture from substrate 120, high pressure values may be used. In general, any characteristic of the fluid jet may be modified to suit its particular purpose (e.g. supplying nutrients, removing cells), such as variations in angle, pressure, volume, etc. These variations may be uniformly applied across the fluid jets, or individual fluid jets may have settings that vary from one another.

Figure 7:
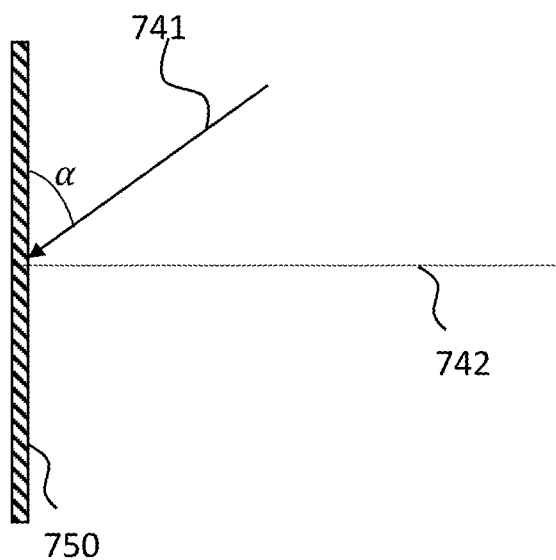
FIG. 7 shows a schematic of fluid jet impinging a substrate at an angle, consistent with disclosed embodiments.

A required pressure or flow rate of fluid delivered through fluid dispenser 134 or 150 may be determined based on adhesive properties of cell culture to substrates 120. For example, FIG. 7 illustrates a jet of fluid (represented by 741) impinging on substrate 750 at an angle α relative to substrate 750. It is contemplated that lower flow rates and/or pressure of fluid may be required to separate the cell culture from substrate 750 as angle α increases from 0° to an angle between 0° and 90° (represented by axis 742). It is contemplated that a maximum rate of separation of the cell culture from substrate 750 may be achieved at an angle α more than 0° and less than 90°. In one exemplary embodiment, angle α may range between 0° and 45°, more preferably between 5° and 45°, and even more preferably between 5° and 30°.

It should be appreciated that depending on the dimensions of substrate 120, only some angles may be realized for fluid jets at some locations of substrates 120. For example, in regions away from the top portion of substrates 120, angles α~0° may only be realized (i.e., fluid jets may be configured to be substantially tangential to surfaces of substrates 120 in those regions).

Figure 8:
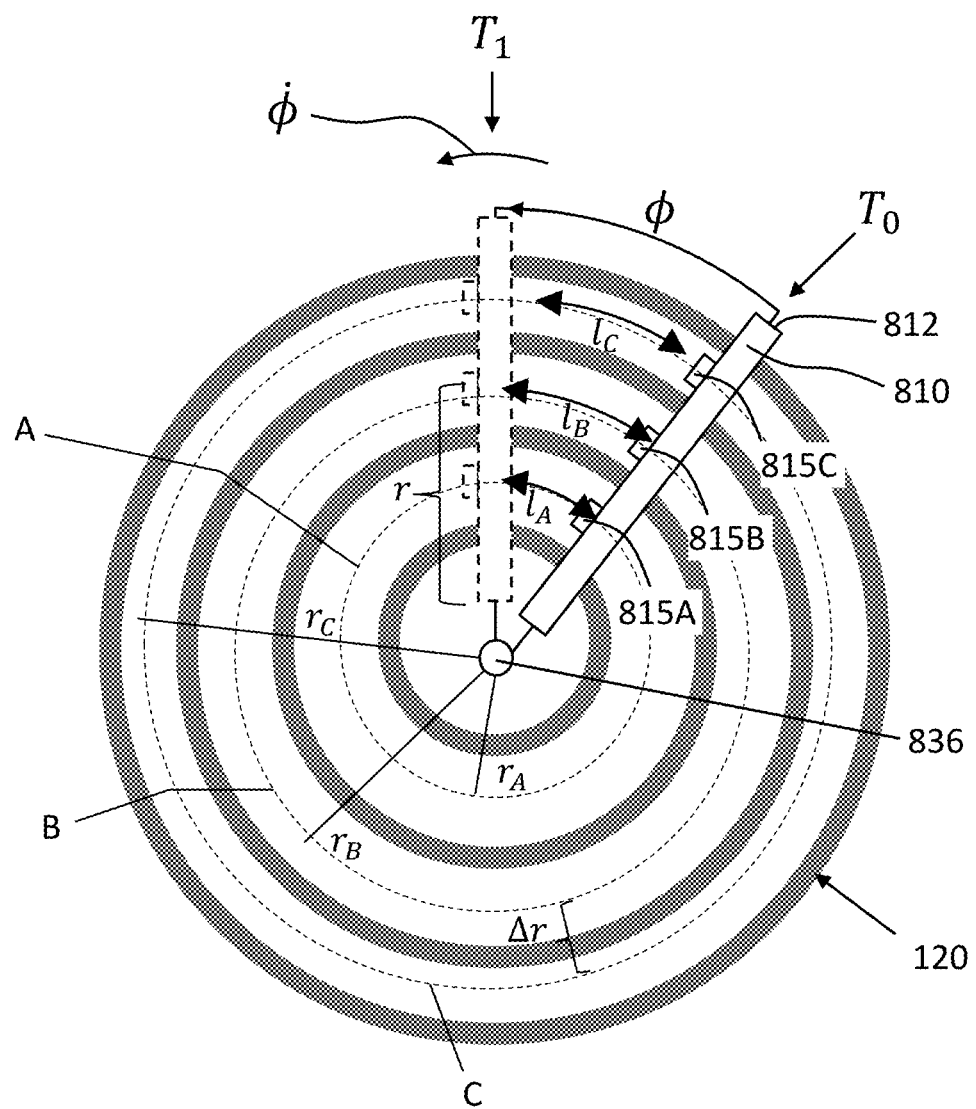
FIG. 8 shows a top view of a portion of a fluid dispenser and a top view of substrates for growing cultured cell sheets, consistent with disclosed embodiments.

FIG. 8 shows a top view of example substrates 120, as well as a top view of a portion 810 of fluid dispenser 134. In an example embodiment, portion 810 may include fluid outlets 815A-815C positioned such that they emit fluid along concentric rings. In one exemplary embodiment, fluid outlets 815A-815C may emit fluid along concentric rings of substrates 120, as shown in FIG. 8. It is contemplated, however, that the arrangement of FIG. 8 may be used with other shapes and sizes of substrates 120. As illustrated in the exemplary embodiment of FIG. 8, when portion 810 rotates by an angle ϕ from a position taken at time $T_0$ to a position taken at time $T_1$, each fluid outlet 815A-815C sweeps out a respective arc length $l_A$, $l_B$, and $l_C$, given respectively by $ϕr_A$, $ϕr_B$, $ϕr_C$ with $r_A$, $r_B$, and $r_C$, being radii of respective circles A, B, and C, as shown in FIG. 8. A radial difference between neighboring circles is conveniently denoted by Δr, as shown in FIG. 8. Although FIG. 8 illustrates only one fluid outlet positioned in each of the gaps between the concentric rings, it is contemplated that in some exemplary embodiments, more than one fluid outlet may be located in the gaps between the concentric rings. It is further contemplated that the plurality of outlets in the gaps between the concentric rings may be oriented at different angles to allow fluid exiting these outlets to impinge on the substrates 120 at different locations or heights (e.g., top, middle, or bottom). Thus, it may be possible to direct the jets of fluid exiting from the outlets on to different regions of substrates 120.

If it is desirable to deliver the same amount of fluid (e.g., same mass flow rate or volume flow rate) per unit of an arc length, then one solution may be to cause fluid outlet 815C to deliver fluid at a larger mass or volume flow rate than fluid outlet 815A or 815B. Similarly, fluid outlet 815B may deliver a larger mass or volume flow rate than fluid outlet 815A. For example, if the volume flow rates for fluid outlets 815A, 815B, 815C are given, respectively, by $q_A$, $q_B$, and $q_C$, then if the same amount of volume flow rate is desired to be delivered per arc length, then $q_A/(\phi r_A) = q_B/(\phi r_B) = q_C/(\phi r_C)$, or equivalently, $q_A/r_A = q_B/r_B = q_C/r_C$. Thus, in an example embodiment, fluid dispenser 134 may be configured such that the volume flow rate emitted from one or more outlets (or from one or more positions of an outlet) is increasing in a direction from center point 836 to an end point 812 linearly as a function of radial distance r. Alternatively, flow velocity may linearly or progressively increase in a direction from center point 836 to an end point 812 as a function of radial distance r, while fluid volume flow rate may remain static or linearly or progressively decrease in the same direction. Other variations of mass or volume flow rate and/or fluid velocity along a length of fluid dispenser 134 or 150 are also contemplated.

Figure 9A:
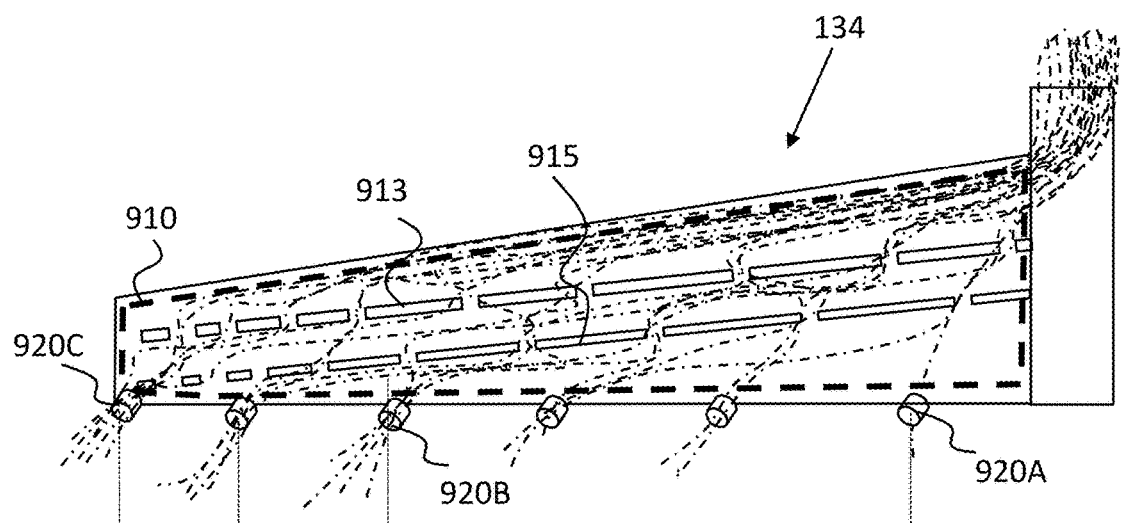
FIG. 9A shows a fluid dispenser having a baffle region, consistent with disclosed embodiments.
Figure 9B:
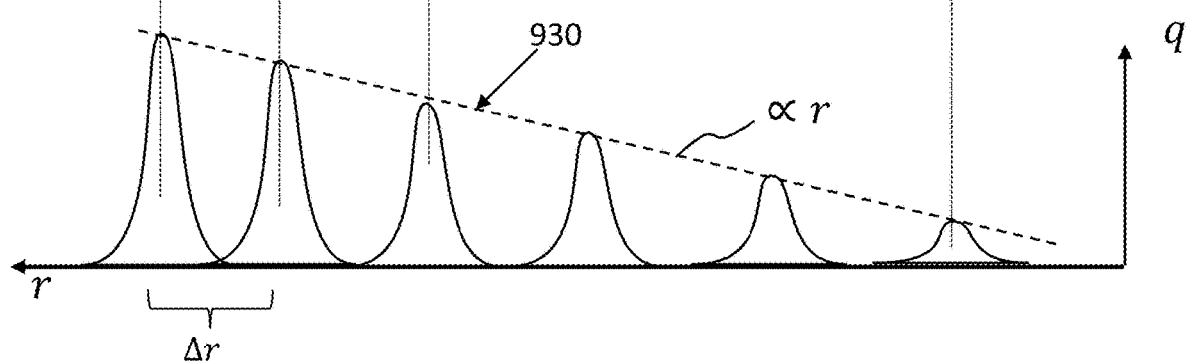
FIG. 9B shows an exemplary distribution of volume flow rate along a length of a fluid dispenser, with the fluid dispenser having the baffle, consistent with disclosed embodiments.

Consistent with described embodiments, a volume flow rate of fluid emitted from fluid dispenser 134 may vary along a length of fluid dispenser 134 (e.g., may vary along a fluid outlet 230A, as shown in FIG. 2A). To achieve the required variation of volume flow rate, various approaches may be employed for designing fluid dispenser 134. An example embodiment of a fluid dispenser 134 is shown in FIG. 9A. Fluid dispenser 134 may include a cavity 910 (herein, also referred to as a baffle 910) that is configured to flow fluid to various fluid outlets, such as outlets 920A-920C. Cavity 910 is the same as cavity 222, as shown in FIGS. 2A, 4A, and 4B. Baffle 910 may be positioned between fluid supply conduit 132, as shown in FIG. 1A, and one or more fluid outlets (e.g., outlets 920A-920C) and may include at least one of an obstruction or an opening configured to distribute the fluid among outlets 920A-920C. In an example embodiment, baffle 910 may include fluid flow controlling elements (herein also referred to as flow resisting elements), such as elements 913 and 915 for controlling fluid flow within cavity 910. Resistive elements may be any suitable elements of any suitable two-dimensional and three-dimensional shapes (e.g., rectangles, triangles, spheres, pyramids, and the like), having surfaces oriented in any suitable way. In an example embodiment, baffle 910 may have a large number of the flow resisting elements in the vicinity of fluid outlet 920A and a smaller number of flow resisting elements in the vicinity of fluid outlet 920C, thus resulting in higher volume flow rates at fluid outlet 920C and lower volume flow rates at fluid outlet 920A. FIG. 9B shows that resistive elements may be selected to result in a substantially linear distribution 930 of peaks of volume flow rates from various fluid outlets, such as outlets 920A-920C. The linear distance between neighboring peaks may be selected to be substantially the same as distance Δr, shown in FIG. 8. In an example configuration, as shown in FIG. 9B, the overall distribution of volume flow rate along length L of fluid dispenser 134 includes peaks and valleys, with peaks matching the radial location of spaces between substrates 120 and valleys matching the radial location of substrates 120.

In some embodiments, baffle 910 may be configured to be completely filled with fluid, and in other embodiments, baffle 910 may include regions containing gas. In some cases, the regions containing gas may be pressurized to result in target pressures within baffle 910.

In various embodiments, a volume flow rate of fluids emitted from fluid dispenser 134 may be a function of time. For example, fluid released by flow outlets 920A-920C may increase or decrease as a function of time or may pulsate as a function of time. In some cases, directions of fluid jets emitted by flow outlets 920A-920C may change as a function of time. For example, when flow outlets 920A-920C correspond to nozzles 511A-511C, thrust vectoring systems corresponding to nozzles 511A-511C may be used to facilitate changes in the direction of nozzles 511A-511C as a function of time. For instance, a suitable controller, as discussed above, may be configured to send electrical signals to one or more electro-mechanical actuators, such as one or more electrical motors of a thrust vector system for nozzle 511A, to change the orientation of nozzle 511A. Additionally, or alternatively, cross-sectional shapes of fluid jets emitted from outlets 920A-920C may change as a function of time. For example, cross-sectional shapes of an example fluid jet may be changed by changing the size or shape of an outlet area of an example outlet (e.g., outlet 920A). The change in size or shape of an outlet area may be achieved using any suitable known approaches such as mechanical diaphragms, valves, and the like.

In some cases, fluid resisting elements such as elements 913 and 915 may be configured to move relative to each other. For instance, baffle 910 may include surfaces containing one or more holes (herein, also referred to as meshes) configured to be movable (e.g., rotatable) relative to each other. In an example embodiment, when holes of a pair of meshes align (e.g., a hole of one mesh is substantially below a hole of another mesh), fluid flow may increase (at a region where the holes are aligned) and may decrease at a region where the holes are misaligned. In various embodiments, meshes may have a non-uniform distribution of holes of variable sizes. In some cases, meshes may extend throughout baffle 910, and in other cases, meshes may be positioned above various flow outlets, such as outlets 920A-920C.

The volume flow rate from various fluid outlets, such as outlets 920A-920C, may be controlled by suitable valves. In an example embodiment, one or more valves may be placed at a fluid outlet to control the volume flow rate from that outlet. One or more valves may allow for a fine volume flow rate control. The valves may be opened or closed using any suitable mechanism (e.g., the valve may be electrically operated). Further, the valves may be controlled by a suitable controller, which may include a computing device having a processor, a memory, as well as one or more sensors for determining various flow parameters related to various fluid outlets (e.g., flow parameters may include the direction of flow from the fluid outlets, volume flow rates from the fluid outlets, cross-sectional shapes of fluid jets from the fluid outlets, and the like), as well as parameters related to a position and an angular velocity of fluid dispenser 134. Further, the controller may include instructions for controlling the operation of one or more valves.

In some embodiments, various fluids may be distributed by fluid dispenser 134. For example, fluid dispenser 134 may be configured to distribute water, nutrients dissolved in water, water-based cleaning fluids, or any other suitable liquids. In some embodiments, fluid dispenser 134 may distribute fluids comprising gases (e.g., steam, hot air, nitrogen, oxygen, $CO_2$, or any other suitable gases or combinations thereof). In some embodiments, fluid dispenser 134 may be configured to emit simultaneously several different types of fluids. For example, fluid dispenser 134 may release from a fluid outlet water containing gas bubbles, or it may release from a first outlet a liquid (e.g., water) and from a second fluid outlet a gas (e.g., air). In an example embodiment, when the first outlet is in the proximity of the second outlet, a jet of air may be used to control the spreading and orientation of a jet of water. For example, a jet of air may be used to guide the jet of water towards a particular surface of substrates 120. It should be appreciated that any number of liquid and gas jets may be combined to result in a required distribution of a liquid over a set of surfaces of substrates 120.

Figure 10:
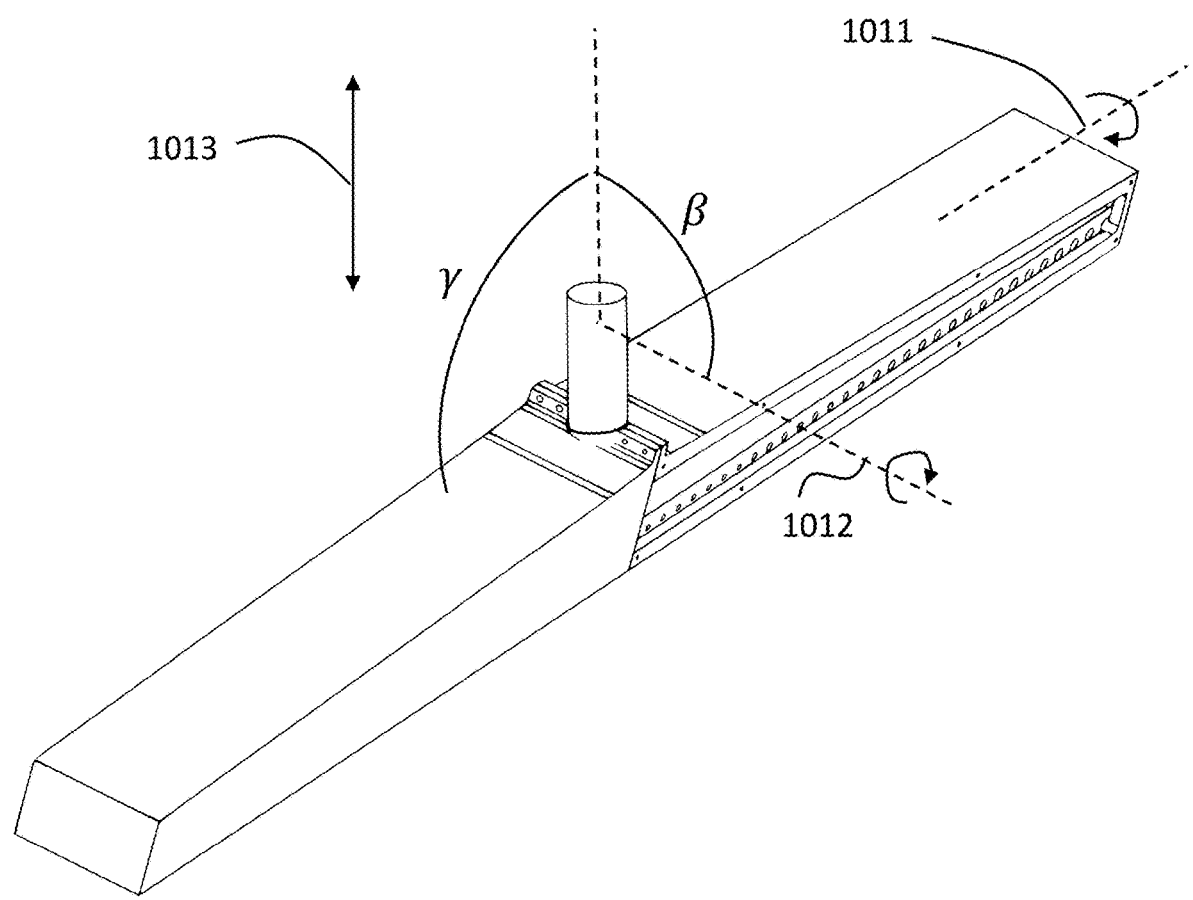
FIG. 10 shows degrees of freedom of a fluid dispenser, consistent with disclosed embodiments.

FIG. 10 shows an example embodiment, in which the entire fluid dispenser 134 has additional degrees of motion via rotation around axis 1011 or axis 1012 by a respective angle β or γ. Such additional degrees of motion may further control directions of fluid flows from fluid dispenser 134. Additionally, or alternatively, fluid dispenser 134 may execute up/down motions as indicated by arrow 1013. For instance, when delivering nutrients to cell culture grown on substrates 120, fluid dispenser 134 may be at a first distance from the top portion of substrates 120, and when using fluid jets for harvesting cell culture from substrates 120 (i.e., removing cell culture from substrates 120), fluid dispenser 134 may be at a second distance from the top portion of substrates 120. In an example embodiment, the first distance may be larger than the second distance.

Consistent with disclosed embodiments, fluid dispenser 134 may operate in several modes. In a first nurturing mode of operation, fluid dispenser 134 may be configured to release nutrients dissolved in a suitable fluid. In such an operational mode, fluid dispensed by fluid dispenser 134 may be in the form of a mist. In the nurturing mode, the fluid flow may be configured to be sufficiently gentle to prevent damage or removal of cell culture grown on substrates 120. In some embodiments, substrates 120 may be immersed in a liquid pool, and liquid containing nutrients may be slowly added to the liquid pool. Alternatively, substrates 120 may be surrounded by gas, and mist jets may be used to deliver nutrients to cell culture grown on surfaces of substrates 120.

In an alternative embodiment, fluid dispenser 134 may operate in a second harvesting mode. In the harvesting mode, high-velocity fluid jets (and/or high-volume flow rate fluid jets) having a required combination of shear and turbulence may be used to remove cell culture from substrates 120. These high-velocity fluid jets may be configured to remove cell culture from some of the surfaces of substrates 120 by directing fluid jets to these surfaces. Alternatively, high-velocity fluid jets may be configured to remove cell culture from all surfaces of substrates 120.

Consistent with another embodiment, fluid dispenser 134 may operate in a third cleaning mode. In the cleaning mode, fluid dispenser 134 may deliver cleaning fluids using any suitable volume flow rate towards substrates 120 and towards internal surfaces of enclosure 111. In some cases, cleaning fluids may include steam, hot air, disinfecting fluids, and the like. Various cleaning fluids may be delivered via high-velocity fluid jets or via mist, as needed. Although fluid dispensers 134, 150 have been described above as being configured to deliver fluid from fluid conduit 132 to enclosure 111, it is contemplated that in some situations, fluid dispensers 134, 150 may allow a reverse flow of liquids or gases. For example, when enclosure 111 is supplied with fluid using a fluid inlet located adjacent to bottom end 151 of enclosure 111, the rising fluid in enclosure 111 may compress the air or gas present in enclosure 111. The compressed air or gas may flow through the openings, outlets, and/or channels of fluid dispensers 134, 150 towards fluid conduit 132 in a reverse flow to be removed from enclosure 111. Similarly, when enclosure 111 is completely filled with fluid, when additional fluid is introduced into enclosure 111 from a fluid inlet located adjacent to bottom end 151, excess fluid in enclosure 111 may flow through the openings, outlets, and/or channels of fluid dispensers 134, 150 towards fluid conduit 132 in a reverse flow to be removed from enclosure 111.

In various embodiments, when transferring from one mode of operation towards another mode of operation, fluid dispenser 134 may be cleaned or rinsed. For example, if fluid dispenser 134 first operates in the cleaning mode and then operates in the nurturing or seeding mode, fluid dispenser 134 may require to be cleaned and/or rinsed prior to operating in the nurturing or seeding mode. In an example embodiment, fluid dispenser 134 may be configured to be removable from enclosure 111 for cleaning and rinsing. For example, fluid dispenser 134 may be moved up and out of enclosure 111, drained, cleaned, rinsed, and/or steamed at a suitable cleaning and rinsing station, and then reinserted into enclosure 111. Such movements of fluid dispenser 134 may be facilitated by a suitable mechanism (e.g., a robotic arm).

Figure 11A:
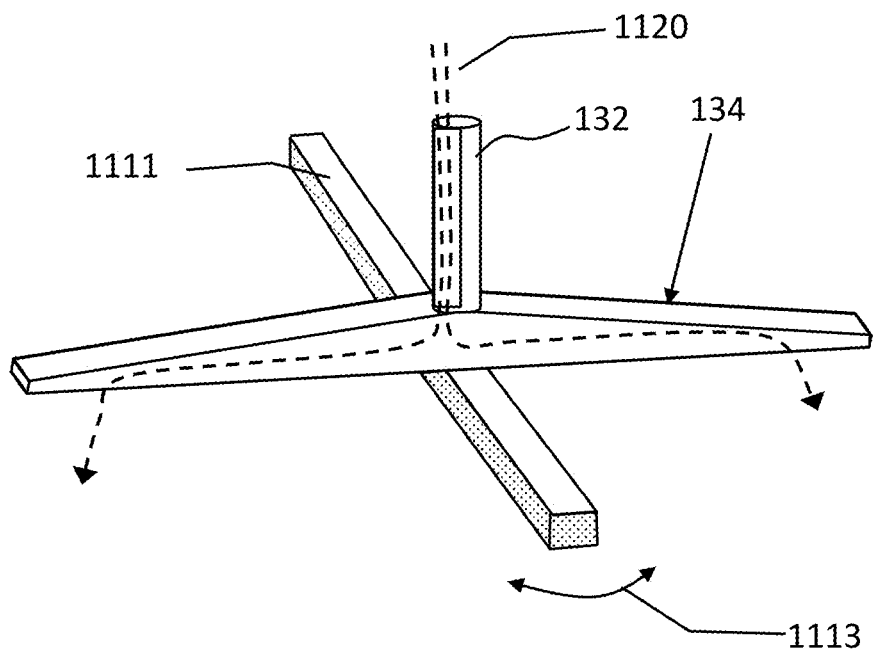
FIGS. 11A and 11B show an example embodiment of a fluid dispenser with a closing element, consistent with disclosed embodiments.
Figure 11B:
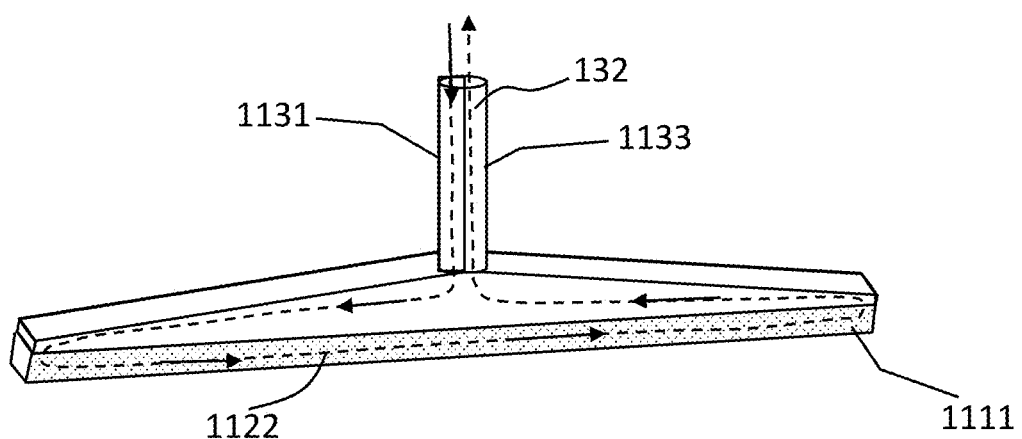

In an alternative embodiment, fluid dispenser 134 may be cleaned and rinsed without being removed from enclosure 111. In order to prevent cleaning and rinsing liquids from entering enclosure 111, fluid dispenser 134 may be configured to encapsulate the cleaning and rinsing liquids. In an example embodiment, shown in FIG. 11A, a closing element 1111 may be configured to be rotated about a vertical axis as shown by arrows 1113 to open or close fluid dispenser 134. When fluid dispenser 134 is open (as shown in FIG. 11A), a flow of fluid, shown by flow lines 1120, is configured to be dispensed by fluid dispenser 134 into enclosure 111. Alternatively, when fluid dispenser 134 is closed (as shown in FIG. 11B) by rotating closing element 1111 so that it is aligned with fluid dispenser 134, fluid entering fluid dispenser 134 first travels through various enclosures and orifices of fluid dispenser 134 that require cleaning or rinsing, and then enters closing element 1111 from which it is configured to be extracted without entering enclosure 111. In an example embodiment, fluid supply conduit may include a channel 1131, as shown in FIG. 11B, configured to deliver fluid to fluid dispenser 134, and a channel 1133 configured to deliver fluid via closing element 1111 out of fluid dispenser 134, as indicated by a flow line 1122. In an example embodiment, when closing element 1111 is oriented as shown in FIG. 11A, channel 1133 is not engaged, and fluid is delivered into enclosure 111. Alternatively, when closing element 1111 closes fluid dispenser 134, channel 1133 is engaged, and fluid is removed from fluid dispenser 134 via channel 1133.

Consistent with disclosed embodiments, system 100 may include various sensors located, for example, within enclosure 111 and configured to provide feedback to a controller on how well fluid dispenser 134 performs any of the three modes of operations described above. In an example embodiment, sensors may include cameras, electrically conductive elements, or any other suitable sensors configured to monitor growth and removal of cell culture as well as cleaning of system 100.

In an example embodiment, a sensor, such as a camera for capturing visible or infrared images, may be configured to monitor growth characteristics of cell culture over substrates 120 and provide feedback to the controller. For example, if a cell culture is not sufficiently grown over at least some substrates 120 (or over some of the regions of substrates 120), a sensor (or several sensors) may provide required feedback that may be used by the controller to add more nutrients to regions in which cell culture is not sufficiently grown.

Consistent with another disclosed embodiment, a sensor (e.g., a camera for capturing visible or infrared images) may be configured to monitor how well cell culture is being removed from substrates 120. For example, if cell culture is not removed from at least some substrates 120 (or from some of the regions of substrates 120), a sensor (or several sensors) may provide required feedback that may be used by the controller to direct high-velocity fluid jets to regions in which cell culture is not removed from substrates 120. In some cases, suitable sensors may measure electrical conductivity through various regions of substrates 120 to determine whether cell culture is removed from these regions. Alternatively, electrical conductivity measurements may be used to determine whether regions of substrates 120 have been sufficiently cleaned. In some cases, sensors may determine reflectivity (e.g., a degree of specular/diffusive reflectivity) of substrates 120 to determine how well substrates 120 are cleaned.

Figure 12:
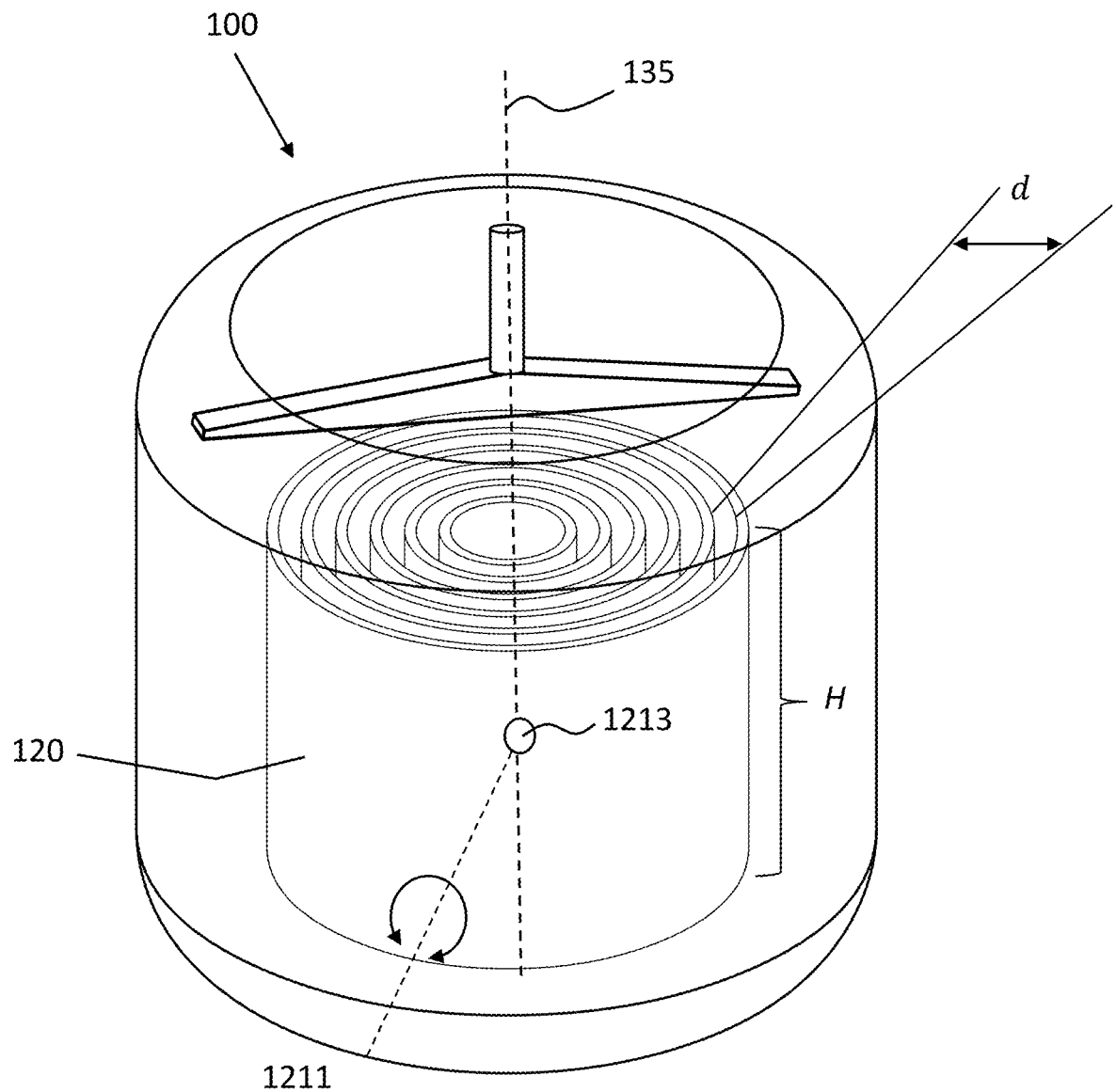
FIG. 12 shows an example embodiment of substrates for growing cultured cell sheets capable of a rotation, consistent with disclosed embodiments.

FIG. 12 shows an example embodiment of system 100 in which substrates 120 may be configured to rotate (as a whole) about axis 1211 perpendicular to axis 135, with axis 1211 passing through a central point 1213 of substrates 120. Such rotation may be beneficial for exposing the bottom portion of substrates 120 to the flow of fluids from fluid dispenser 134. This rotation may allow for symmetric growth of cell culture at the top and the bottom portion of substrates 120, as well as for symmetric removal of cell culture from the top and the bottom portions of substrates 120. In an example embodiment, the top portion of substrates 120 may be exposed to a flow of nutrients from fluid dispenser 134; subsequently, substrates 120 may be rotated by 180 degrees around axis 1211 such that the bottom portion of substrates 120 is exposed to a flow of nutrients from fluid dispenser 134. Consistent with another embodiment, the top portion of substrates 120 may be exposed to high-velocity fluid jets such that cell culture is removed from the top portion of substrates 120; subsequently, substrates 120 may be rotated by 180 degrees around axis 1211 such that the bottom portion of substrates 120 is exposed to high-velocity fluid jets for removal of cell culture from the bottom portion of substrates 120. In various embodiments, a height H, and a distance d as shown in FIG. 12, for substrates 120 may be selected to allow for uniform growth and removal of cell culture from substrates 120 using the fluid flow from fluid dispenser 134. Such selection may be achieved, for example, via experimentation.

It should be appreciated that substrates 120 may undergo other movements besides rotation about axis 1211. For instance, substrates 120 may be configured to be rotated about vertical axis 135 or configured to execute vibrational motions (e.g., vibrational rotational motions around axis 135, vibrational lateral motions, or vibrational vertical motions to facilitate removal of cell culture from surfaces of substrates 120).

The foregoing description has been presented for purposes of illustration. It is not exhaustive and is not limited to precise forms or embodiments disclosed. Modifications and adaptations of the embodiments will be apparent from a consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application; such examples are to be construed as nonexclusive.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents which may be resorted to fall within the scope of the disclosure.

Other embodiments will be apparent from a consideration of the specification and practice of the embodiments disclosed herein. It is intended that the specification and examples be considered as an example only, with a true scope and spirit of the disclosed embodiments being indicated by the following claims.

What is claimed is:

1. An assembly for delivering a fluid to seed, grow, or harvest a cell-based comestible meat product, the assembly comprising:
   a fluid dispenser connected to a fluid supply conduit, the fluid dispenser comprising:
   multiple fluid outlets positioned along a length of the fluid dispenser, wherein the length of the fluid dispenser is rotatable relative to the fluid supply conduit;
   a baffle positioned within an interior of the length of the fluid dispenser, the baffle comprising multiple flow resisting surfaces arranged in multiple rows to vary fluid flow rates between the multiple fluid outlets to create a linear distribution of peaks of volume flow rates along the length of the fluid dispenser; and
   an electronic controller coupled to at least one fluid outlet of the multiple fluid outlets and configured to adjust at least one of an orientation, a shape, or a size of the at least one fluid outlet.

2. The assembly of claim 1, wherein adjusting the at least one fluid outlet changes a flow configuration of a fluid exiting the at least one fluid outlet between a first flow pattern and a second flow pattern, the second flow pattern having a higher fluid velocity than the first flow pattern.

3. The assembly of claim 1, wherein the peaks of volume flow rates are aligned with radial locations of spaces between a plurality of substrates configured to receive fluid dispersed from the multiple fluid outlets of the fluid dispenser.

4. The assembly of claim 1, wherein the peaks of volume flow rates from the multiple fluid outlets increase in a direction from an axis of rotation of the fluid dispenser towards a distal end of the fluid dispenser.

5. The assembly of claim 4, wherein a volume flow rate per unit of an arc length traveled by each fluid outlet of the multiple fluid outlets as the length of the fluid dispenser rotates relative to the fluid dispenser is constant between the multiple fluid outlets.

6. The assembly of claim 1, further comprising multiple openings between the multiple flow resisting surfaces of the baffle.

7. The assembly of claim 6, wherein a height of the baffle decreases along the length of the fluid dispenser.

8. The assembly of claim 6, wherein the multiple openings between the multiple flow resisting surfaces are offset between the multiple rows.

9. The assembly of claim 6, wherein a number of openings between the multiple flow resisting surfaces increases in a direction from an axis of rotation of the fluid dispenser towards a distal end of the fluid dispenser.

10. The assembly of claim 1, wherein at least one row of the multiple rows has a central axis such that an angle between a normal direction to the multiple fluid outlets and the central axis is substantially different from ninety degrees.

11. The assembly of claim 1, comprising at least a first channel and a second channel configured to supply fluid to the fluid dispenser, wherein a first amount of fluid discharged from the first channel is configured to rotate the fluid dispenser in a clockwise direction, and wherein a second amount of fluid discharged from the second channel is configured to rotate the fluid dispenser in a counter-clockwise direction.

12. The assembly of claim 1, wherein one of a motor or the fluid discharged from the multiple fluid outlets is configured to rotate the fluid dispenser.

13. The assembly of claim 1, wherein a first fluid outlet of the multiple fluid outlets proximate to an axis of rotation of the fluid dispenser has a first width and a second fluid outlet of the multiple fluid outlets proximate to a distal end of the fluid dispenser has a second width different than the first width.

14. The assembly of claim 13, wherein the second width is larger than the first width.

15. The assembly of claim 2, wherein the electronic controller is further configured to change the flow configuration of the fluid exiting the at least one fluid outlet to a third flow pattern that allows for harvesting of adhered cells from substrate surfaces.

16. The assembly of claim 15, wherein the third flow pattern has a higher fluid velocity than the second flow pattern.

17. The assembly of claim 15, wherein the electronic controller is further configured to deliver the fluid via the at least one fluid outlet at the third flow pattern that allows for harvesting of the adhered cells by delivering the fluid in a fluid jet.

18. The assembly of claim 15, wherein the electronic controller is further configured to tailor the third flow pattern based on adhesive properties of the adhered cells.

19. The assembly of claim 2, wherein the electronic controller is further configured to deliver the fluid via the at least one fluid outlet at the second flow pattern that delivers nutrients to and promotes growth of adhered cells by delivering the fluid as a mist.

20. The assembly of claim 1, wherein the electronic controller comprises a computing device programmed to do one or more of:
- determine a position and an angular velocity of the fluid dispenser,
- determine a speed and a direction of rotation of the fluid dispenser, or
- provide commands to a motor that is configured to rotate the fluid dispenser.

* * * * *